United States Patent
Smithey et al.

(10) Patent No.: US 8,974,823 B2
(45) Date of Patent: Mar. 10, 2015

(54) SOLID COMPOSITIONS OF LOW-SOLUBILITY DRUGS AND POLOXAMERS

(75) Inventors: Daniel Tod Smithey, Bend, OR (US); Dwayne Thomas Friesen, Bend, OR (US); Warren Kenyon Miller, Bend, OR (US); Walter Christian Babcock, Bend, OR (US)

(73) Assignee: Bend Research, Inc., Bend, OR (US)

( * ) Notice: Subject to any disclaimer, the term of this patent is extended or adjusted under 35 U.S.C. 154(b) by 1625 days.

(21) Appl. No.: 10/596,876

(22) PCT Filed: Dec. 20, 2004

(86) PCT No.: PCT/IB2004/004287
§ 371 (c)(1),
(2), (4) Date: Nov. 28, 2006

(87) PCT Pub. No.: WO2005/065657
PCT Pub. Date: Jul. 21, 2005

(65) Prior Publication Data
US 2007/0141143 A1   Jun. 21, 2007

Related U.S. Application Data

(60) Provisional application No. 60/533,836, filed on Dec. 31, 2003.

(51) Int. Cl.
*A61K 9/20* (2006.01)
*A61K 9/16* (2006.01)
*A61K 9/50* (2006.01)

(52) U.S. Cl.
CPC .............. *A61K 9/1635* (2013.01); *A61K 9/1641* (2013.01); *A61K 9/5084* (2013.01)
USPC ......................................................... 424/464

(58) Field of Classification Search
USPC ......................................................... 424/464
See application file for complete search history.

(56) References Cited

U.S. PATENT DOCUMENTS

| | | | |
|---|---|---|---|
| 6,248,363 B1 | 6/2001 | Patel et al. | 424/497 |
| 6,264,981 B1 | 7/2001 | Zhang et al. | 424/451 |
| 6,316,029 B1 | 11/2001 | Jain et al. | 424/484 |
| 6,368,622 B2 | 4/2002 | Chen et al. | 424/464 |
| 6,395,300 B1 | 5/2002 | Straub et al. | 424/489 |
| 6,763,607 B2 * | 7/2004 | Beyerinck et al. | 34/372 |
| 2001/0036959 A1 | 11/2001 | Gabel et al. | 514/411 |
| 2001/0053778 A1 * | 12/2001 | Hoover et al. | 514/227.8 |
| 2001/0053791 A1 * | 12/2001 | Babcock et al. | 514/419 |
| 2002/0006951 A1 | 1/2002 | Hageman et al. | 514/406 |
| 2002/0012704 A1 | 1/2002 | Pace et al. | 424/489 |
| 2002/0040051 A1 | 4/2002 | Lee et al. | 514/456 |
| 2003/0054042 A1 * | 3/2003 | Liversidge et al. | 424/489 |

FOREIGN PATENT DOCUMENTS

| | | | | |
|---|---|---|---|---|
| EP | 1103258 | 5/2001 | | A61K 31/19 |
| EP | 0836475 | 11/2001 | | A61K 9/14 |
| WO | WO 9702017 | 1/1997 | | A61K 9/14 |
| WO | WO 9921534 | 5/1999 | | A61K 9/14 |
| WO | WO 0134118 | 5/2001 | | A61K 9/14 |
| WO | WO 0134119 | 5/2001 | | A61K 9/14 |
| WO | WO 0147495 | 7/2001 | | A61K 9/14 |
| WO | WO 0154667 | 8/2001 | | A61K 9/14 |
| WO | WO 0174357 | 10/2001 | | A61K 9/14 |
| WO | WO 0180828 | 11/2001 | | A61K 9/00 |
| WO | WO 0197853 | 12/2001 | | A61K 47/12 |
| WO | WO 0211694 | 2/2002 | | A61K 9/00 |
| WO | WO 0213790 | 2/2002 | | A61K 9/10 |
| WO | WO 02/089835 A2 * | 11/2002 | | |

OTHER PUBLICATIONS

Muller et al. ("Nanosuspensions as particulate drug formulations in therapy: Rationale for development and what we can expect for the future," in Advanced Drug Delivery Reviews vol. 47, Issue 1, Mar. 23, 2001, pp. 3-19—Nanoparticulate Systems for Improved Drug Delivery).*

Rogers et al. ("Enhanced Aqueous Dissolution of a Poorly Water Soluble Drug by Novel Particle Engineering Technology: Spray-Freezing into Liquid with Atmospheric Freeze-Drying," in Pharmaceutical Research, vol. 20, No. 3, Mar. 2003; pp. 465-493).*

X. Xu and P.I. Lee, "*Programmable Drug Delivery from an Erodible Association Polymer System*", Pharmaceutical Research, 10:8(1993), pp. 1144-1152.

* cited by examiner

*Primary Examiner* — Blessing M Fubara
(74) *Attorney, Agent, or Firm* — Klarquist Sparkman, LLP

(57) ABSTRACT

Solid compositions of low-solubility drugs and poloxamers that provide concentration enhancement when administered to an aqueous environment of use are disclosed.

13 Claims, No Drawings

SOLID COMPOSITIONS OF LOW-SOLUBILITY DRUGS AND POLOXAMERS

CROSS REFERENCE TO RELATED APPLICATION

This application is a National Stage filing of PCT Application PCT/IB2004/004287 filed Dec. 20, 2004, which claims the benefit of priority of U.S. provisional Patent Application Ser. No. 60/533,836 filed Dec. 31, 2003.

FIELD OF THE INVENTION

This invention relates to solid compositions of low-solubility drugs and poloxamers that maintain physically stability and concentration enhancement of dissolved drug when administered to an aqueous environment of use.

BACKGROUND OF THE INVENTION

It is sometimes desired to form a composition of amorphous drug and a polymer. One reason for forming such compositions is that the aqueous concentration of a poorly soluble drug may be improved by such a technique. For example, EP 0 901 786 A2 to Curatolo et al. discloses forming pharmaceutical spray-dryed dispersions of sparingly soluble drugs and the polymer hydroxypropyl methyl cellulose acetate succinate, in which the drug is amorphous and dispersed in the polymer. The spray-dried dispersions disclosed in Curatolo et al. provide superior aqueous concentration relative to dispersions formed from other methods and relative to the crystalline drug alone.

Similarly, others have recognized the enhancement in aqueous concentration afforded by forming compositions of a drug in a polymer. U.S. Pat. No. 5,456,923 to Nakamichi et al. discloses solid dispersions formed by twin-screw extrusion of low solubility drugs and various polymers.

Poloxamers (polyoxyethylene-polyoxypropylene copolymers) are routinely used in the pharmaceutical arts for a variety of applications, primarily as emulsifying agents in intravenous fat emulsions, and as solubilizing and stabilizing agents to maintain the clarity of elixirs and syrups. Poloxamers are also used as wetting agents; in ointments, suppository bases, and gels; and as tablet binders and coatings.

Forming compositions of poloxamers and drugs is known. U.S. Pat. No. 6,368,622 to Chen et al. discloses a mixture of drug with a poloxamer. In a particular embodiment, the drug fenofibrate, having a melting point of 72° to 82° C. and a glass transition temperature ($T_g$) of about −19° C., is melted with a poloxamer. While the data show the drug in the composition has a faster dissolution rate than a commercial formulation, no concentration enhancement was demonstrated.

U.S. Patent Application Publication No. US2001/0036959A1 to Gabel et al. discloses a composition comprising the drug carvedilol, having a melting point of 113° to 116° C. and a $T_g$ of about 39° C., in a concentration above 5 wt %. The preparation preferably includes poloxamers. The composition may be formed using a melt method or by spray-drying.

European Patent Specification EP 0836475B1 to Clancy et al. discloses a solid composition of an active ingredient in a hydrophilic poloxamer polymer. The composition is formed either by melting the poloxamer and dispersing the active ingredient therein or dissolving the active ingredient and poloxamer in an organic solvent or solvents; the solvent is evaporated and the molten poloxamer is cooled and milled to obtain the formulation.

However, a problem with forming solid compositions containing amorphous drug and a substantial amount of poloxamer is that the drug can crystallize over time, leading to poor performance. Thus, there is a continuing need to provide methods and formulations for enhancing the concentration of low-solubility drugs while providing physical stability.

SUMMARY OF THE INVENTION

In a first aspect, the invention comprises a solid composition comprising a plurality of particles. The particles comprise a low-solubility drug and a poloxamer. The drug is in intimate contact with the poloxamer in the particles. Collectively, the drug and poloxamer constitute at least 50 wt % of the particles. At least a substantial portion of the drug in the composition is amorphous. The $T_g$ of the drug is at least 50° C. Unless otherwise noted, as used herein the $T_g$ refers to the $T_g$ measured at less than 10% RH. The composition provides concentration enhancement of the low-solubility drug when administered to an in vitro or in vivo aqueous environment of use.

In a second aspect, the invention comprises a solid composition comprising a plurality of particles. The particles comprise a low-solubility drug and a poloxamer. The drug is in intimate contact with the poloxamer in the particles. Collectively, the drug and poloxamer constitute at least 50 wt % of the particles. At least a substantial portion of the drug in the composition is amorphous. The drug has a Log P value of greater than about 6.5. The composition provides concentration enhancement of the low-solubility drug when administered to an in vitro or in vivo aqueous environment of use.

In a third aspect, the invention comprises (1) particles comprising a low-solubility drug and a poloxamer and (2) a concentration-enhancing polymer. The concentration-enhancing polymer is present in a sufficient amount such that the pharmaceutical composition, following administration to an in vivo or in vitro aqueous environment of use, provides concentration enhancement relative to a control composition consisting essentially of the particles comprising the drug and poloxamer.

In a fourth aspect, the invention provides a process for preparing a solid composition comprising the steps of (1) forming a solution consisting essentially of a low-solubility drug, a poloxamer, and a solvent; and (2) removing the solvent from the solution to form solid particles comprising a low-solubility drug and a poloxamer, wherein at least a substantial portion of the drug in the particles is amorphous, and the $T_g$ of the drug is at least 50° C. The solid composition provides concentration enhancement of the low-solubility drug when administered to an in vitro or in vivo aqueous environment of use. In a preferred embodiment, the solvent is removed from the solution by a spray-drying, spray-coating, rotoevaporation or evaporation.

The various aspects of the present invention provide a solid composition comprising a poloxamer that provides both good physical stability as well as improved concentration of dissolved drug in a use environment. Poloxamers are block copolymers consisting of polyethylene oxide (PEO) segments and polypropylene oxide (PPO) segments. Poloxamers have melting points from about 45° to about 60° C. Without wishing to be bound by theory, it is believed that at ambient temperatures, typically 10° to 30° C., the PEO segments will eventually aggregate and crystallize to form semicrystalline PEO domains while the PPO segments will remain as amorphous domains. These PPO domains have a relatively low $T_g$ of about −65° C. As a result, any solute dispersed in the amorphous PPO domains will have high mobility at normal storage temperatures of 5° to 40° C. When drug is dispersed in poloxamers, and subsequently the poloxamer is brought to a temperature below its melting point, the PEO segments will generally crystallize, and drug will primarily reside in the amorphous PPO domains, where the drug will generally have high mobility. The $T_g$ of the drug/PPO domains will generally lie between that of the pure PPO domains and that of pure amorphous drug. The precise value of the $T_g$ of such domains will also depend upon the relative amounts of drug and PPO in the domains, and to a lesser extent, upon the interaction between the drug and the PPO. The inventors have discovered that when the $T_g$ of the drug/PPO domains is less than the storage temperature and the concentration of drug in the PPO domains is above its solubility in the PPO domain, the drug will have a tendency, over time, to crystallize and the amorphous compositions will therefore become unstable.

To reduce this instability, the inventors have discovered that the physical stablility of solid compositions of low-solubility drugs and poloxamers can be improved by choosing the drug to have either (1) a $T_g$ of at least about 50° C., or (2) a Log P value of greater than about 6.5, or both. Solid compositions comprising a low-solubility drug having at least one of these properties and a poloxamer can have higher drug loadings (that is, the fraction of drug in the solid composition can be higher) and/or improved physical stability at storage conditions than solid compositions made with drugs that do not have these properties. The solid compositions also provide concentration enhancement in an aqueous environment of use.

The foregoing and other objectives, features, and advantages of the invention will be more readily understood upon consideration of the following detailed description of the invention.

DETAILED DESCRIPTION OF THE PREFERRED EMBODIMENTS

The present invention relates to solid compositions of a low-solubility drug and a poloxamer. The solid compositions of the present invention are capable of achieving high concentrations of dissolved drug in in vitro and in vivo use environments. The solid compositions provide good physical stability, meaning that the drug in the solid compositions tends to remain in the amorphous form over time at ambient storage conditions. The nature of the solid compositions, suitable poloxamers and low-solubility drugs, methods for making the compositions, and methods for determining concentration enhancement are discussed in more detail below.

Poloxamers

The solid compositions of the present invention comprise a polyoxyethylene-polyoxypropylene block copolymer, also known in the pharmaceutical arts as a "poloxamer." Poloxamers are crystalline or semi-crystalline materials that generally have a molecular weight ranging from about 2000 to about 15,000 daltons and have the general formula:

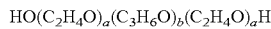

wherein a is about 10 to about 150, representing blocks of repeat units of polyethylene oxide or polyoxyethylene (referred to herein as the PEO segment), and b is about 20 to about 60, representing blocks of repeat units of polypropylene oxide or polyoxypropylene (referred to herein as the PPO segment), depending on the particular grade. Suitable poloxamers are sold under the trade names PLURONIC and LUTROL, both available from BASF Corporation of Mt. Olive, N.J. Preferred poloxamers have a molecular weight of at least about 4,700 daltons and a melting point of at least about 45° C. when dry and so are solid at ambient temperatures.

Preferred grades of poloxamers include poloxamer 188 (PLURONIC F68), poloxamer 237 (PLURONIC F87), poloxamer 338 (PLURONIC F108), poloxamer 407 (PLURONIC F127), the specifications of which are given in Table A, and mixtures of those poloxamers.

TABLE A

| Poloxamer | Physical Form at 25° C. | a | b | Average Molecular Weight (daltons) |
|---|---|---|---|---|
| 188 | Solid | 80 | 27 | 7,680-9,510 |
| 237 | Solid | 64 | 37 | 6,840-8,830 |
| 338 | Solid | 141 | 44 | 12,700-17,400 |
| 407 | Solid | 101 | 56 | 9,840-14,600 |

Solid Particles of Drug and Poloxamer

The particles of drug and poloxamer are solid at temperatures up to 30° C. and less than 10% relative humidity (RH). In order to keep the total mass of the composition small, it is preferred that the particle comprise at least about 5 wt % drug. More preferably, the particle comprises at least about 10 wt % drug, and more preferably at least about 20 wt % drug. In one embodiment, the particle has a high drug loading. Drug loading refers to the weight fraction of drug in the solid composition. In this embodiment, the drug may be present in an amount of at least about 40 wt % of the particle, at least about 45 wt %, or may even be at least about 50 wt %. Such high loadings of drug are desirable to keep the total mass of the pharmaceutical composition at a low value. High drug loadings are possible for physically stable compositions which have either a high $T_g$ (>50° C.) or a drug having a high Log P, as described more fully below.

At least a substantial portion of the drug in the particles is amorphous. By "amorphous" is meant that the drug is in a non-crystalline state. As used herein, the term "a substantial portion" of the drug means that at least 75 wt % of the drug in the particles is in the amorphous form, rather than the crystalline form. It has been found that the aqueous concentration of the drug in a use environment tends to improve as the fraction of drug present in the amorphous state increases. Accordingly, a "substantial portion" of the drug in the particles is amorphous, and preferably the drug is "almost completely amorphous," meaning that the amount of drug in the crystalline form does not exceed 10 wt %. Amounts of crystalline drug may be measured by powder X-ray diffraction (PXRD), Scanning Electron Microscope (SEM) analysis, differential scanning calorimetry (DSC), or any other standard quantitative measurement. Most preferably the dispersion is substantially free of crystalline drug.

The amorphous drug in the particles is in intimate contact with the poloxamer. The amorphous drug in the particle can exist as a pure phase, as a solid solution of drug homogeneously distributed throughout the poloxamer, or any combination of these states or those states that lie between them. Without wishing to be bound by any theory, it is believed that the two different block portions of the poloxamer, e.g. the PEO and PPO segments of the poloxamer, are present as different phases in each of the particles. As noted above, the PEO portion may be semi-crystalline, such as in the form of lamellar sheets, and as such, contains little if any of the drug. The other phase is composed of amorphous PPO with all or part of the drug homogeneously dissolved in the-PPO; ln some cases, particularly at high drug loading, a third phase may exist, consisting primarily of amorphous drug within the particle. Thus, the drug may be present primarily in the PPO portion, and may be homogeneously distributed throughout the PPO portion, or the drug may be present as drug-rich domains interspersed throughout the particle, or may be in any combination of these two states or those states that lie between them. In cases where drug-rich amorphous domains exist, these domains are generally quite small; that is, less than about 1 µm in size. Preferably, such domains are less than about 100 nm in size. The particles may have a single $T_g$, indicating that the drug is homogeneously dispersed throughout the poloxamer, or may have two $T_g$s, corresponding to a drug-rich phase and a drug-poor amorphous phase. Thus, while the drug in the particles is amorphous, a portion of the poloxamer in the particles may be in a crystalline or semi-crystalline state. Analysis of the particles of the present invention by PXRD or other quantitative methods for determining the crystallinity of a material will typically indicate peaks associated with crystalline or semi-crystalline poloxamer.

Solid compositions of the present invention provide good physical stability. As used herein, "physically stable" or "physical stability" means the tendency of the amorphous drug present in the particles to crystallize at ambient storage conditions of 25° C. and less than 10% RH. Thus, a solid composition that is more physically stable than another will have a slower rate of drug crystallization in the solid composition. Specifically, compositions of this invention have sufficient stability that less than about 10 wt % of the drug crystallizes during storage for 3 weeks at 25° C. and 10% RH. Preferably, less than about 5 wt % of the drug crystallizes during storage for 3 weeks at 25° C. and 10% RH, and more preferably, after storage for 3 months at 25° C. and 10% RH.

Without wishing to be bound by any particular theory or mechanism of action, it is believed that physically stable particles containing both drug and poloxamer generally fall into two categories: (1) those that are thermodynamically stable (in which there is little or no driving force for crystallization of the amorphous drug) and (2) those that are kinetically stable or metastable (in which a driving force exists for crystallization of the amorphous drug but low drug mobility prevents or slows the rate of crystallization to an acceptable level).

To achieve thermodynamically stable solid compositions, the solubility of the amorphous drug in the poloxamer should be approximately equal to or greater than the drug loading. By drug loading is meant the weight fraction of drug in the solid particles. The particles may have a drug loading that is slightly higher than the solubility and still be physically stable since the driving force for crystal nucleation in that case is quite low. By "slightly higher" is meant a drug loading 10 to 20% higher than the solubility of the drug in the poloxamer. The solubility of the drug in the amorphous form of the poloxamer generally increases as the hydrophobicity of the drug increases. A common measure of hydrophobicity is Log P, defined as the base 10 logarithm of the ratio of the drug solubility in octanol to the drug solubility in water. Log P may be measured experimentally or calculated using methods known in the art. Calculated Log P values are often referred to by the calculation method, such as Clog P, Alog P, and Mlog P. The inventors believe that the higher the Log P of a drug, the higher will be its solubility in the poloxamer and, in turn, the higher the drug loading may be in the solid particles and still be physically stable. Specifically when the Log P of the low-solubility drug is greater than about 4.5, the drug loading of the composition may be up to about 30 wt %; when the Log P is greater than about 5.5, the drug loading may be up to about 40 wt %, and when the Log P is greater than about 6.5, the drug loading may be up to about 50 wt %.

Solid compositions of low solubility drugs and poloxamers, wherein the drug has a relatively high Log P value, may have higher drug loadings and still be physically stable because the solubility of the drug in the poloxamer is higher relative to compositions containing drugs with a lower Log P. Thus, the maximum drug loading that a composition may have and still be thermodynamically stable increases with increasing Log P of the drug. It should be noted that the solubility of a drug in poloxamer is, in addition to being a function of the Log P of the drug, also a function of the melting point $(T_m)$ of the drug. In general, for a given Log P value, the solubility of the drug in the poloxamer decreases with increasing melting point of the drug above the storage temperature. Thus, for compositions of two drugs with Log P equal to 6.5, one with a $T_m$ of about 80° C. and the other drug with a $T_m$ of about 120° C., the solubility of the first drug in the poloxamer will generally be higher than the second drug and therefore amorphous compositions of the first drug may have higher drug loadings and still have acceptable physical stability.

When the drug loading in the particles is 10 to 20% percent greater than the solubility of the drug in the poloxamer (that is, the solid composition is supersaturated in amorphous drug), the particles are not thermodynamically stable and a driving force exists for phase separation of the amorphous drug into a drug-rich phase. Such drug-rich phases may be amorphous and microscopic (less than about 1 µm in size), or amorphous and relatively large (greater than about 1 µm in size) or crystalline in nature. Thus, following phase separation, the compositions can consist of two or three phases: (1) a drug-rich phase comprising primarily drug; (2) a phase comprising amorphous drug dispersed in the poloxamer; and (3) an optional phase comprising semi-crystalline PEO segments of the poloxamer. The amorphous drug in the drug-rich phases can over time convert from the amorphous form to the lower-energy crystalline form. The physical stability of such particles will generally be greater, for a given drug loading, (1) the lower the molecular mobility of the amorphous drug, and (2) the lower the tendency for the amorphous drug to crystallize from the drug-rich phases.

Molecular mobility is generally lower and physically stability greater for particles composed of drug with a high $T_g$ value. The $T_g$ of the drug-containing phase(s) is a measure of the molecular mobility of the drug in the particle. The higher the $T_g$ of the drug-containing phase, the lower the mobility of the drug. Thus, the ratio of the $T_g$ of the drug-containing phase to the storage temperature $(T_{storage})$ for the drug-containing phases of the particle (in K) is an accurate indicator of the relative drug mobility at a given storage temperature. In order to minimize phase separation, it is desired that the mobility of the amorphous drug in the particle be low. This is accomplished by maintaining a ratio of $T_g$ of the particle/$T_{storage}$ of greater than about 1. Since typical storage temperatures can be as high as 40° C., it is preferred that the $T_g$s of the particles be at least about 40° C., more preferably at least about 45° C., and most preferably at least about 50° C. Since the $T_g$s are a function of the water content of the particles, which in turn is a function of the relative humidity to which the particles are exposed, these $T_g$ values refer to the $T_g$ of the particles that has been equilibrated with an atmosphere that has a low relative humidity, that is, less than about 10% of saturation (or an RH of about 10% or less).

As noted above, a portion of the poloxamer may in the compositions be crystalline or semi-crystalline. Suitable pharmaceutical grades of poloxamers have melting points between about 45° C. to about 60° C. Because the poloxamer in the composition may have a melting point in this range, it may be difficult to verify that the $T_g$ of the particles is also in this same range by using standard thermal methods such as DSC since the melt exotherm of the semi-crystalline portion of the poloxamer occurs at about the same temperature as the $T_g$.

The inventors have found that the $T_g$ of the drug alone may be used as a good indicator of the physical stability of particles which have drug loadings that substantially exceed the drug's solubility in the poloxamer. This is especially true for particles in which the $T_g$ of the drug-containing phase is near the melting point of the poloxamer, which makes measuring the $T_g$ of the drug-containing phase difficult. Specifically, the inventors have found that a low-solubility drug having a $T_g$ of at least about 50° C. generally results in physically stable solid compositions. Without wishing to be bound by any particular theory, it is believed that the higher the $T_g$ of the drug is, the higher the $T_g$s of the amorphous drug-containing phases of the solid composition will be, and the lower the molecular mobility of the amorphous drug in the solid composition will be. As a result, solid compositions formed with low-solubility drugs having high $T_g$ values and poloxamers tend to have high $T_g$ values themselves, and as a result, improved physical stability. Such $T_g$ values may represent that of drug dispersed in the amorphous portions of the poloxamer or the $T_g$ of drug-rich phases or domains. In the case of drug-rich domains, the $T_g$ is generally about that of the drug alone. In the case of drug dispersed in the poloxamer, the $T_g$ generally lies between those of the drug alone and the poloxamer alone. Thus, the higher the $T_g$ of the drug, the higher the $T_g$s of the solid composition, and therefore, the greater the physical stability of the solid composition. The $T_g$ of the drug may be at least about 60° C., at least about 70° C., or even at least about 80° C. The $T_g$ of a drug can be determined using standard analytical techniques well known in the art, including by a dynamic mechanical analyzer (DMA), a dilatometer, a dielectric analyzer, and by differential scanning calorimetry (DSC).

In addition, the melting point of the drug, $T_m$, may also be used as an indicator of the physical stability of the solid composition. In general, drugs with higher melting points tend to have higher glass transition temperatures as well, and may therefore have improved kinetic stability. Thus, in one embodiment, the drug may have a melting point of at least 130° C., at least 140° C., or even at least 150° C. The $T_m$ can be determined using standard analytical techniques well known in the art, such as those described above for measuring $T_g$.

However, physical stability is also related to the relative difference between the $T_m$ and the $T_g$ of a drug. Although the primary indicator of the physical stability of amorphous drug-poloxamer compositions with drug loadings substantially in excess of the amorphous drug solubility in the poloxamer is the $T_g$ of the drug, the tendency of the drug to crystallize also has an effect on the physical stability of such compositions. Without wishing to be bound by any particular theory, it is believed that the tendency for amorphous drug to crystallize when a drug-rich phase is formed is characterized by the ratio of the $T_m$ of the drug to the drug's $T_g$ (both in ° K). The driving force for crystallization is dominated by the $T_m$, and the kinetic barrier to crystallization is controlled primarily by the $T_g$. The ratio $T_m/T_g$ indicates the relative propensity for a drug to crystallize. Thus, for a series of hypothetical drugs with equivalent $T_g$ values of about 60° C., amorphous composition of a drug with a $T_m/T_g$ value of about 1.30 will be more physically stable than an equivalent composition with a drug that has a $T_g$ value of about 1.35, which in turn will be more stable than an equivalent composition with a $T_m/T_g$ value of about 1.40.

Since conversion of amorphous drug in the particles to the crystalline state is related to the relative values of (1) the $T_g$ of the particles, (2) $T_{storage}$, and (3) relative humidity, the drug in the particles may tend to remain in the amorphous state for longer periods when stored at ambient temperature (less than 40° C.) and low relative humidity (less than 10% RH). In addition, packaging of such solid compositions so as to prevent absorption of water or inclusion of a water absorbing material such as a desiccant to also prevent or retard water absorption can maintain a high $T_g$ for the particles during storage, thereby helping to retain the amorphous state. Likewise, storage at lower temperatures can also improve the retention of the amorphous state.

The primary constituents of the particles are the low-solubility drug and the poloxamer. The drug and poloxamer together constitute at least 50 wt % of the particles. The drug and poloxamer may constitute even greater amounts of the composition, and may constitute at least 60 wt %, at least 70 wt %, at least 80 wt %, or even at least 90 wt % of the particles. In one embodiment, the particles consist essentially of the low-solubility drug and poloxamer.

The amount of drug relative to the amount of poloxamer present in the particles of the present invention depends on the characteristics of the drug and poloxamer and may vary widely from a drug-to-poloxamer weight ratio of from about 0.01 to about 100 (e.g., 1 wt % drug to 99 wt % drug). Preferably, the drug-to-poloxamer weight ratio ranges from about 0.05 to about 49 (5 wt % drug to 98 wt % drug). The amount of poloxamer in the particles will depend on the dose of the drug, the stability of the resulting particles, and the degree of concentration enhancement provided by the particles. In one embodiment, the poloxamer is present in the particles in an amount that is greater than any other non-drug excipient. Typically, the poloxamer is present from at least 40 wt % up to 99 wt % of the particles.

Low-Solubility Drugs

The term "drug" is conventional, denoting a compound having beneficial prophylactic and/or therapeutic properties when administered to an animal, especially humans. Preferably, the drug is a "low-solubility drug," meaning that the drug has a minimum aqueous solubility at physiologically relevant pH (i.e., pH 1-8) of about 0.5 mg/mL or less. The invention finds greater utility as the aqueous solubility of the drug decreases. Thus, compositions of the present invention are preferred for low-solubility drugs having an aqueous solubility of less than about 0.1 mg/mL, more preferably less than about 0.05 mg/mL, and most preferably less than about 0.01 mg/mL. In general, it may be said that the drug has a dose-to-aqueous solubility ratio greater than about 10 mL, and more typically greater than about 100 mL, where the aqueous solubility (mg/mL) is the minimum value observed in any physiologically relevant aqueous solution (i.e., pH 1-8), including USP simulated gastric and intestinal buffers, and dose is in mg. Thus, a dose-to-aqueous solubility ratio may be calculated by dividing the dose (in mg) by the aqueous solubility (in mg/mL).

Preferred classes of drugs include, but are not limited to, antihypertensives, antianxiety agents, anticlotting agents, anticonvulsants, blood glucose-lowering agents, decongestants, antihistamines, antitussives, antineoplastics, beta blockers, anti-inflammatories, antipsychotic agents, cognitive enhancers, cholesterol-reducing agents, anti-atherosclerotic agents, antiobesity agents, autoimmune disorder agents, anti-impotence agents, antibacterial and antifungal agents, hypnotic agents, anti-Parkinsonism agents, anti-Alzheimer's disease agents, antibiotics, anti-depressants, antiviral agents, glycogen phosphorylase inhibitors, and cholesteryl ester transfer protein inhibitors.

As described above, in one aspect the drug has a $T_g$ of at least about 50° C. Exemplary drugs that have a $T_g$ of at least about 50° C. are shown below in Table B.

Methods for Making Particles of Drug and Poloxamer

The particles of drug and poloxamer of the present invention may be made according to any known process that results in at least a substantial portion, that is, at least 75 wt % of the drug being in the amorphous state. Such processes include solvent and thermal processes. In thermal processes, a molten mixture of the low-solubility drug and poloxamer is rapidly cooled such that the molten mixture rapidly solidifies. In solvent processes, the low-solubility drug and poloxamer are dissolved in a common solvent and the solvent subsequently removed by evaporation or by mixing with a non-solvent.

The particles of drug and poloxamer are well-suited for formation by solvent processes. The high $T_g$ of the solid

TABLE B

| Drug Name | $T_g$ (° C.) | $T_m$ (° C.) |
|---|---|---|
| (+)-2-(3-benzyl-4hydroxy-chroman-7-yl)-4-trifluoromethyl-benzoic acid | 53 | 145 |
| quinoxaline-2-carboxylic acid [4(R)-carbamoyl-1(S)-3-fluorobenzyl)-2(S),7-dihydroxy-7-methyl-octyl]amide | 69 | 165 |
| Ziprasidone (5-(2-(4-(3-benzisothiazolyl)-piperazinyl)ethyl-6-chlorooxindole) | 72 | 224 |
| [R—(R*,S*)]-5-chloro-N-[2-hydroxy-3-[(methoxymethylamino)-3-oxo-1-(phenylmethyl)propyl]propyl]-1H-indole-2-carboxamide | 80 | 190 |
| 4-[3-[4-(2-methylimidazol-1-yl) phenylthio] phenyl]-3,4,5,6-tetrahydro-2H-pyran-4-carboxamide hemifumarate | 81 | 228 |
| [3,6-dimethyl-2-(2,4,6-trimethyl-phenoxy)-pyridin-4-yl]-(1-ethyl-propyl)-amine hydrochloride | 87 | 225 |
| 5-chloro-1H-indole-2-carboxylic acid [(1)-benzyl-2-(3-hydroxy-azetidin-1-yl)-2-oxo-ethyl]-amide | 91 | 175 |
| 5-chloro-1H-indole-2-carboxylic acid [(1S)-benzyl-(2R)-hydroxy-3-((3R,4S)-dihydroxy-pyrrolidin-1-yl-)-3-oxypropyl]amide | 96 | 238 |
| 2-phenanthrenecarboxamide,4b,5,6,7,8,8a,9,10-octahydro-7-hydroxy-N-[(2-methyl-3-pyridinyl)methyl]-4b-(phenylmethyl)-7-(3,3,3-trifluoropropyl)-, (4bS,7S,8aR)- | 99 | 225 |
| 2-(4-fluorophenyl)-beta, delta-dihydroxy-5-(1-methylethyl)-3-phenyl-4-[(phenylamino)carbonyl]-1H-pyrrole-1-heptanoic acid, calcium salt (2:1), trihydrate | 111 | |
| (2(-(4-((4-chlorophenyl)phenylmethyl)-1-piperazinyl)ethoxy)acetic acid, dihrochloride | 112 | |
| N-(1,1-dimethylethyl) decahydro-2-[(2R,3R)-2-hydroxy-3-[(3-hydroxy-2-methylbenzoyl) amino]-4-(phenylthio) butyl]-3-isoquinolinecarboxamide (3s, 4aS, 8aS)-monomethanesulfonate | 116 | 190 |
| 1-[4-ethoxy-3-(6,7-dihydro-1-methyl-7-oxo-3-propyl-1H-pyrazolo[4,3-d]pyrimidin-5-yl)phenylsulphonyl]-4-methylpiperazine | 135 | 193 |
| 3-[(4-O-{4,6-bis(2-flurophenylcarbamoyl)]-β-D-glucopyranolsyl-)β-D-flucopyranosyl]oxy-(3β,5α,25R)-spirostan-12-one | 143 | 250 |

In another embodiment, the drugs have a log P of greater than about 6.5. Exemplary drugs having a Log P value of greater than about 6.5 are shown below in Table C.

compositions of the present invention allow for selection of processing conditions that lead to formation of solid materials with a minimum of phase separation of the drug from the

TABLE C

| NAME | Log P |
|---|---|
| 1-[4-ethoxy-3-(6,7-dihydro-1-methyl-7-oxo-3-propyl-1H-pyrazolo[4,3-d]pyrimidin-5-yl)phenylsulphonyl]-4-methylpiperazine | 7.0 |
| [3,6-dimethyl-2-(2,4,6-trimethyl-phenoxy)-pyridin-4-yl]-(1-ethyl-propyl)-amine | 7.0 |
| 2R,4S] 4-[(3,5-bis-trifluoromethyl-benzyl)-methoxycarbonyl-amino]-2-ethyl-6-trifluoromethyl-3,4-dihydro-2H-quinoline-1-carboxylic acid isopropyl ester | 7.8 |
| [2R,4S] 4-[(3,5-bis-trifluoromethyl-benzyl)-methoxycarbonyl-amino]-2-ethyl-6-trifluoromethyl-3,4-dihydro-2H-quinoline-1-carboxylic acid ethyl ester | 7.3 |
| [2R,4S] 4-[acetyl-(3,5-bis-trifluoromethyl-benzyl)-amino]-2-ethyl-6-trifluoromethyl-3,4-dihydro-2H-quinoline-1-carboxylic acid isopropyl ester | 6.9 |
| (2R)-3-[[3-(4-chloro-3-ethylphenoxy)phenyl][[3-(1,1,2,2-tetrafluoroethoxy)phenyl]methyl]amino]-1,1,1-trifluoro-2-propanol | 10.1 | poloxamer. By "phase separation" is meant that a significant amount of the drug in the composition separates into domains rich in amorphous drug. When phase separation does occur and drug-rich domains form, choosing conditions where solvent is removed rapidly causes the domains to be quite small—generally less than about 1 µm in size and preferably less than 200 nm in size. For those embodiments where the $T_m/T_{g,drug}$ ratio is less than about 1.4, the reduced tendency of the drug to crystallize allows for formation of particles by solvent processing wherein at least a substantial portion of the drug in the particles is amorphous. While thermal processes can be used to prepare the particles of the present invention, in cases where the $T_m$ of the low-solubility drug is high, processing at high temperatures is generally less desirable as degradation of the drug, the poloxamer, or both are more likely to occur. Thus, formation of the particles via solvent processing is preferred.

In solvent processes, the low-solubility drug and poloxamer are dissolved in a common solvent. "Common" here means that the solvent, which can be a mixture of compounds, will dissolve both the drug and the polymer. After both the drug and the polymer have been dissolved, the solvent is removed by evaporation or by mixing with a non-solvent. Exemplary processes are spray-drying, spray-coating (pan-coating, fluidized bed coating, etc.), rotoevaporation, and precipitation by rapid mixing of the polymer and drug solution with $CO_2$, water, or some other non-solvent. Preferably, removal of the solvent results in the formation of a substantially homogeneous phase of amorphous drug in the PPO portion of the poloxamer.

Solvents suitable for solvent processing are preferably volatile, having a boiling point of 150° C. or less. In addition, the solvent should have relatively low toxicity and be removed from the particles to a level that is acceptable according to The International Committee on Harmonization (ICH) guidelines. Removal of solvent to this level may require a subsequent processing step such as tray drying. Preferred solvents include water; alcohols such as methanol, and ethanol; ketones such as acetone, methyl ethyl ketone and methyl iso-butyl ketone; and various other solvents such as acetonitrile, methylene chloride, and tetrahydrofuran. Lower volatility solvents such as dimethyl acetamide or dimethylsulfoxide can also be used in small amounts in mixtures with a volatile solvent. Mixtures of solvents, such as 50% methanol and 50% acetone, can also be used, as can mixtures with water, so long as the polymer and drug are sufficiently soluble to make the process practicable. Generally, due to the hydrophobic nature of low-solubility drugs, non-aqueous solvents are preferred, meaning that the solvent comprises less than about 30 wt % water.

The solvent may be removed by spray-drying. The term "spray-drying" is used conventionally and broadly refers to processes involving breaking up liquid mixtures into small droplets (atomization) and rapidly removing solvent from the mixture in a spray-drying apparatus where there is a strong driving force for evaporation of solvent from the droplets. Spray-drying processes and spray-drying equipment are described generally in Perry's *Chemical Engineers' Handbook*, pages 20-54 to 20-57 (Sixth Edition 1984). More details on spray-drying processes and equipment are reviewed by Marshall, "Atomization and Spray-Drying," 50 *Chem. Eng. Prog. Monogr. Series* 2 (1954), and Masters, *Spray Drying Handbook* (Fourth Edition 1985). The strong driving force for solvent evaporation is generally provided by maintaining the partial pressure of solvent in the spray-drying apparatus well below the vapor pressure of the solvent at the temperature of the drying droplets. This is accomplished by (1) maintaining the pressure in the spray-drying apparatus at a partial vacuum (e.g., 0.01 to 0.50 atm); or (2) mixing the liquid droplets with a warm drying gas; or (3) both (1) and (2). In addition, at least a portion of the heat required for evaporation of solvent may be provided by heating the spray solution.

The solvent-bearing feed, comprising the drug and the poloxamer, can be spray-dried under a wide variety of conditions and yet still yield particles with acceptable properties. For example, various types of nozzles can be used to atomize the spray solution, thereby introducing the spray solution into the spray-dry chamber as a collection of small droplets. Essentially any type of nozzle may be used to spray the solution as long as the droplets that are formed are sufficiently small that they dry sufficiently (due to evaporation of solvent) that they do not stick to or coat the spray-drying chamber wall.

Although the maximum droplet size varies widely as a function of the size, shape and flow pattern within the spray-dryer, generally droplets should be less than about 500 µm in diameter when they exit the nozzle. Examples of types of nozzles that may be used to form the solid compositions include the two-fluid nozzle, the fountain-type nozzle, the flat fan-type nozzle, the pressure nozzle and the rotary atomizer. In a preferred embodiment, a pressure nozzle is used, as disclosed in detail in commonly assigned copending U.S. application Ser. No. 10/351,568, the disclosure of which is incorporated herein by reference.

The spray solution can be delivered to the spray nozzle or nozzles at a wide range of temperatures and flow rates. Generally, the spray solution temperature can range anywhere from just above the solvent's freezing point to about 20° C. above its ambient pressure boiling point (by pressurizing the solution) and in some cases even higher. Spray solution flow rates to the spray nozzle can vary over a wide range depending on the type of nozzle, spray-dryer size and spray-dry conditions such as the inlet temperature and flow rate of the drying gas. Generally, the energy for evaporation of solvent from the spray solution in a spray-drying process comes primarily from the drying gas.

The drying gas can, in principle, be essentially any gas, but for safety reasons and to minimize undesirable oxidation of the drug or other materials in the solid composition, an inert gas such as nitrogen, nitrogen-enriched air or argon is utilized. The drying gas is typically introduced into the drying chamber at a temperature between about 60° and about 300° C. and preferably between about 80° and about 240° C.

The large surface-to-volume ratio of the droplets and the large driving force for evaporation of solvent leads to rapid solidification times for the droplets. Solidification times should be less than about 20 seconds, preferably less than about 10 seconds, and more preferably less than 1 second. This rapid solidification is often critical to the particles maintaining a uniform, homogeneous phase of amorphous drug and the PPO portion. In a preferred embodiment, the height and volume of the spray-dryer are adjusted to provide sufficient time for the droplets to dry prior to impinging on an internal surface of the spray-dryer, as described in detail in commonly assigned, copending U.S. application Ser. No. 10/353,746, the disclosure of which is incorporated herein by reference.

Following solidification, the solid powder typically stays in the spray-drying chamber for about 5 to 60 seconds, further evaporating solvent from the solid powder. The final solvent content of the particles as they exit the dryer should be low, since this reduces the mobility of the drug molecules in the particles, thereby improving its stability. Generally, the solvent content of the particles as they leave the spray-drying chamber should be less than 10 wt % and preferably less than 2 wt %. Following formation, the particles can be dried to remove residual solvent using suitable drying proceses, such as tray drying, fluid bed drying, microwave drying, belt drying, rotary drying, vacuum drying, and other drying processes known in the art.

In another embodiment, the particles are formed by a rotoevaporation process. In this process the drug and poloxamer are dissolved in a common solvent as described above. The solvent is then removed by rotoevaporation to form the solid composition. The resulting thick syrup or solids may then be dried on a high vacuum line. The resulting solids are preferably formed into small particles, such as by using a mortar and pestle or other milling processes known in the art. The particles may be sieved and dried as necessary to obtain a material with the desired properties.

In another embodiment, the particles are formed by spraying a coating solution of the drug and poloxamer onto seed cores. The seed cores can be made from any suitable material such as starch, microcrystalline cellulose, sugar or wax, by any known method, such as melt- or spray-congealing, extrusion/spheronization, granulation, spray-drying and the like.

The coating solution can be sprayed onto such seed cores using coating equipment known in the pharmaceutical arts, such as pan coaters (e.g., Hi-Coater available from Freund Corp. of Tokyo, Japan, Accela-Cota available from Manesty of Liverpool, U.K.), fluidized bed coaters (e.g., Würster coaters or top-sprayers available from Glatt Air Technologies of Ramsey, N.J. and from Niro Pharma Systems of Bubendorf, Switzerland) and rotary granulators (e.g., CF-Granulator, available from Freund Corp).

While solvent processes are preferred for formation of the particles of the present invention, thermal processes, such as melt-congeal or melt-extrusion processes, may also be used. In such processes, a molten mixture of the low-solubility drug and poloxamer is rapidly cooled such that the molten mixture rapidly solidifies. By "molten mixture" is meant a mixture comprising the low-solubility drug and poloxamer that is fluid in the sense that it will flow when subjected to one or more forces such as pressure, shear, and centrifugal force. This generally requires that the mixture be heated to a temperature at which the drug either melts or dissolves into the molten poloxamer. The low-solubility drug can exist in the molten mixture as a pure phase, as a solution of low-solubility drug homogeneously distributed throughout the molten mixture, or any combination of these states or those states that lie intermediate between them. The molten mixture is preferably substantially homogeneous so that the low-solubility drug is dispersed as homogeneously as possible throughout the molten mixture. Preferably, the molten mixture is formed using an extruder, such as a single-screw or twin-screw extruder, both well known in the art.

Generally, the processing temperature may vary from about 50° C. up to about 200° C. or higher, depending on the melting point of the low-solubility drug and poloxamer. However, the processing temperature should not be so high that an unacceptably high level of degradation of the drug or poloxamer occurs. In some cases, the molten mixture should be formed under an inert atmosphere to prevent degradation of the drug and/or poloxamer at the processing temperature. When relatively high temperatures are used, it is often preferable to minimize the time that the mixture is at the elevated temperature to minimize degradation.

The molten mixture may also comprise an excipient that will reduce the melting temperature of the molten mixture, allowing processing at lower temperature. For example, a volatile agent that dissolves or reduces the melting point of the drug can be included in the molten mixture. Exemplary volatile excipients include acetone, water, methanol, and ethyl acetate. When such volatile excipients are added the excipients evaporate or are otherwise removed from the particles in the process of or following conversion of the molten mixture to a solid mixture. In such cases, the processing may be considered to be a combination of solvent processing and melt-congealing or melt-extrusion. Removal of such volatile excipients from the molten mixture can be accomplished by breaking up or atomizing the molten mixture into small droplets and contacting the droplets with a fluid such that the droplets both cool and lose all or part of the volatile excipient.

Once the molten mixture of low-solubility drug and poloxamer is formed, the mixture should be rapidly solidified to form the particles. By "rapidly solidified" is meant that the molten mixture is solidified sufficiently fast such that substantial phase separation of the drug and polymer does not occur. Typically, this means that the mixture should be solidified in less than about 10 minutes, more preferably in less than about 5 minutes, and most preferably in less than about 1 minute. If the mixture is not rapidly solidified, phase separation can occur, resulting in the formation of low-solubility drug-rich phases having a large domain size of greater than one micron and poloxamer-rich phases. Over time, the drug in the low-solubility drug-rich phases can crystallize. Such compositions tend not to perform as well as those compositions that are rapidly solidified. Solidification often takes place primarily by cooling the molten mixture to at least about 10° C. and preferably at least about 30° C. below its melting point. As mentioned above, solidification can be additionally promoted by evaporation of all or part of one or more volatile excipients or solvents. To promote rapid cooling and evaporation of volatile excipients, the molten mixture is often formed into a high surface area shape such as a rod or fiber or droplets. For example, the molten mixture can be forced through one or more small holes to form long thin fibers or rods or may be fed to a device, such as an atomizer such as a rotating disk, that breaks the molten mixture up into droplets from 1 μm to 1 cm in diameter. The droplets are then contacted with a relatively cool fluid such as air or nitrogen to promote cooling and evaporation.

The mean size of the particles may be less than 500 μm in diameter, or less than 100 μm in diameter, less than 50 μm in diameter or less than 25 μm in diameter. When the particles are formed by spray-drying, the resulting particles may range in size from 1 μm to 100 μm. When the solid composition is formed by other methods such by spray coating, rotoevaporation, evaporation, melt-congeal, or extrusion processes, the resulting particles may be sieved, ground, or otherwise processed to yield a plurality of small particles.

Once the particles comprising the drug and poloxamer have been formed, several processing operations can be used to facilitate incorporation of the particles into a dosage form. These processing operations include drying, granulation, and milling.

The particles may be granulated to increase their size and improve handling of the particles while forming a suitable dosage form. Preferably, the average size of the granules will range from 50 to 1000 μm. Such granulation processes may be performed before or after the composition is dried, as described above. Dry or wet granulation processes can be used for this purpose. An example of a dry granulation process is roller compaction. Wet granulation processes can include so-called low shear and high shear granulation, as well as fluid bed granulation. In these processes, a granulation fluid is mixed with the composition after the dry components have been blended to aid in the formation of the granulated composition. Examples of granulation fluids include water, ethanol, isopropyl alcohol, n-propanol, the various isomers of butanol, and mixtures thereof. A polymer may be added with the granulation fluid to aid in granulating the particles. Examples of suitable polymers include more poloxamer, hydroxypropyl cellulose, hydroxyethyl cellulose, and hydroxypropyl methylcellulose.

If a wet granulation process is used, the granulated composition is often dried prior to further processing. Examples of suitable drying processes to be used in connection with wet granulation are the same as those described above. Where the solid composition is made by a solvent process, the composition can be granulated prior to removal of residual solvent. During the drying process, residual solvent and granulation fluid are concurrently removed from the composition.

Once the composition has been granulated, it may then be milled to achieve the desired particle size. Examples of suitable processes for milling the composition include hammer milling, ball milling, fluid-energy milling, roller milling, cutting milling, and other milling processes known in the art.

Mixtures of Particles and Concentration-Enhancing Polymers

A separate embodiment of the invention comprises a combination of (1) particles comprising a low-solubility drug and a poloxamer, and (2) a concentration-enhancing polymer. By "concentration-enhancing polymer" is meant a polymer that, when combined with the particles of drug and poloxamer and administered to an aqueous environment of use, increases the concentration of the low-solubility drug in the use environment or the bioavailability of the drug relative to the particles alone. "Combination" in reference to drug, poloxamer and concentration-enhancing poloxamer means that the particles and concentration-enhancing polymer may be in physical contact with each other or in close proximity but without being physically mixed at the molecular level (i.e., a dispersion). The particles and concentration-enhancing polymer may be in different regions of the composition. For example, the particles may be in the form of a multi-layer tablet, as known in the art, wherein one or more layers comprises the amorphous drug and poloxamer and one or more different layers comprises the concentration-enhancing polymer. Yet another example may constitute a coated tablet wherein either the particles or the concentration-enhancing polymer or both may be present in the tablet core and the coating may comprise the concentration-enhancing polymer. Alternatively, the combination can be in the form of a simple dry physical mixture wherein both the particles and the concentration-enhancing polymer are mixed in particulate form and wherein the particles of each, regardless of size, retain the same individual physical properties that they exhibit in bulk. Any conventional method used to mix the particles and concentration-enhancing polymer together such as physical mixing and dry or wet granulation, which does not convert the particles and the concentration-enhancing polymer to molecular dispersion, may be used. Examples include V-blenders, planetary mixers, vortex blenders, mills, extruders such as twin-screen extruders and trituration processes. The ingredients can be combined in granulation processes utilizing mechanical energy, such as ball mills or roller compactors. They may also be combined using wet granulation methods, in high-shear granulators or fluid bed granulators wherein a solvent or wetting agent is added to the ingredients during the granulation process.

Alternatively, the particles and concentration-enhancing polymer may be co-administered, meaning that the particles may be administered separately from, but within the same general time frame as, the concentration-enhancing polymer. Thus, the particles may, for example, be administered in their own dosage form that is taken at approximately the same time as the concentration-enhancing polymer, which is in a separate dosage form. If administered separately, it is generally preferred to administer both the particles and the concentration-enhancing polymer within 60 minutes of each other, so that the two are present together in the use environment. When not administered approximately simultaneously (e.g., within a minute or two of each other), the concentration-enhancing polymer is preferably administered prior to the particles.

The amount of concentration-enhancing polymer present in the composition is sufficient to provide concentration enhancement, as described below. In general, the ratio of drug in the particles to the concentration-enhancing polymer may range from 0.01 (1 part drug to 100 parts polymer) to 100. Preferably, the drug to concentration-enhancing polymer ratio ranges from about 0.66 to about 49, and more preferably from about 3 to about 19, and even more preferably from about 5 to about 15.

Concentration-enhancing polymers suitable for use in the present invention should be pharmaceutically acceptable, and should have at least some solubility in aqueous solution at physiologically relevant pHs (e.g. 1-8). Almost any neutral or ionizable polymer that has an aqueous-solubility of at least 0.1 mg/mL over at least a portion of the pH range of 1-8 may be suitable. In a preferred embodiment, the concentration-enhancing polymer is "amphiphilic" in nature, meaning that the polymer has hydrophobic and hydrophilic portions. Amphiphilic polymers are preferred because it is believed that such polymers tend to have relatively strong interactions with the drug and may promote the formation of various types of polymer/drug assemblies in solution.

One class of polymers suitable for use with the present invention comprises non-ionizable (or neutral) non-cellulosic polymers. Exemplary polymers include: vinyl polymers and copolymers having substituents of hydroxyl, alkylacyloxy, or cyclicamido; polyvinyl alcohols that have at least a portion of their repeat units in the unhydrolyzed (vinyl acetate) form; polyvinyl alcohol polyvinyl acetate copolymers; polyvinyl pyrrolidone; polyoxyethylene-polyoxypropylene copolymers, also known as poloxamers; and polyethylene polyvinyl alcohol copolymers. Exemplary non-cellulosic, neutral polymers include hydroxyethyl methacrylate, polyvinylhydroxyethyl ether, and polyethylene glycol.

Another class of polymers suitable for use with the present invention comprises ionizable non-cellulosic polymers. Exemplary polymers include: carboxylic acid-functionalized vinyl polymers, such as the carboxylic acid functionalized polymethacrylates and carboxylic acid functionalized polyacrylates such as the EUDRAGITS® manufactured by Rohm Tech Inc., of Maiden, Massachusetts; amine-functionalized polyacrylates and polymethacrylates; proteins; and carboxylic acid functionalized starches such as starch glycolate.

Another class of polymers suitable for use with the present invention comprises ionizable and neutral cellulosic polymers with at least one ester- and/or ether-linked substituent in which the polymer has a degree of substitution of at least 0.1 for each substituent. Exemplary non-ionizable cellulosic polymers include: hydroxypropyl methyl cellulose acetate, hydroxypropyl methyl cellulose, hydroxypropyl cellulose, methyl cellulose, hydroxyethyl methyl cellulose, hydroxyethyl cellulose acetate, and hydroxyethyl ethyl cellulose.

Exemplary ionizable cellulosic polymers include: hydroxypropyl methyl cellulose acetate succinate, hydroxypropyl methyl cellulose succinate, hydroxypropyl cellulose acetate succinate, hydroxyethyl methyl cellulose succinate, hydroxyethyl cellulose acetate succinate, hydroxypropyl methyl cellulose phthalate, hydroxyethyl methyl cellulose acetate succinate, hydroxyethyl methyl cellulose acetate phthalate, carboxyethyl cellulose, carboxymethyl cellulose, carboxymethylethyl cellulose, cellulose acetate phthalate, methyl cellulose acetate phthalate, ethyl cellulose acetate phthalate, hydroxypropyl cellulose acetate phthalate, hydroxypropyl methyl cellulose acetate phthalate, hydroxypropyl cellulose acetate phthalate succinate, hydroxypropyl methyl cellulose acetate succinate phthalate, hydroxypropyl methyl cellulose succinate phthalate, cellulose propionate phthalate, hydroxypropyl cellulose butyrate phthalate, cellulose acetate trimellitate, methyl cellulose acetate trimellitate, ethyl cellulose acetate trimellitate, hydroxypropyl cellulose acetate trimellitate, hydroxypropyl methyl cellulose acetate trimellitate, hydroxypropyl cellulose acetate trimellitate succinate, cellulose propionate trimellitate, cellulose butyrate trimellitate, cellulose acetate terephthalate, cellulose acetate isophthalate, cellulose acetate pyridinedicarboxylate, salicylic acid cellulose acetate, hydroxypropyl salicylic acid cellulose acetate; ethylbenzoic acid cellulose acetate, hydroxypropyl ethylbenzoic acid cellulose acetate, ethyl phthalic acid cellulose acetate, ethyl nicotinic acid cellulose acetate, and ethyl picolinic acid cellulose acetate.

While specific polymers have been discussed as being suitable for use in the compositions of the present invention, blends of such polymers may also be suitable. Thus the term "polymer" is intended to include blends of polymers in addition to a single species of polymer.

Preferably, the concentration-enhancing polymer is selected from the group consisting of hydroxypropyl methyl cellulose acetate succinate, hydroxypropyl methyl cellulose phthalate, cellulose acetate phthalate, cellulose acetate trimellitate, carboxymethyl ethylcellulose, and mixtures thereof.

Concentration Enhancement

The solid compositions of the present invention are concentration-enhancing. The term "concentration-enhancing" means that the poloxamer is present in a sufficient amount in the composition so as to improve the concentration of the drug in a use environment relative to a control composition. As used herein, a "use environment" can be either the in vivo environment of the GI tract, subdermal, intranasal, buccal, intrathecal, ocular, intraaural, subcutaneous spaces, vaginal tract, arterial and venous blood vessels, pulmonary tract or intramuscular tissue of an animal, such as a mammal and particularly a human, or the in vitro environment of a test solution, such as phosphate buffered saline (PBS) or a Model Fasted Duodenal (MFD) solution. Concentration enhancement may be determined through either in vitro dissolution tests or through in vivo tests. It has been determined that enhanced drug concentration in in vitro dissolution tests in Model Fasted Duodenal (MFD) solution or Phosphate Buffered Saline (PBS) is a good indicator of in vivo performance and bioavailability. An appropriate PBS solution is an aqueous solution comprising 20 mM sodium phosphate ($Na_2HPO_4$), 47 mM potassium phosphate ($KH_2PO_4$), 87 mM NaCl, and 0.2 mM KCl, adjusted to pH 6.5 with NaOH. An appropriate MFD solution is the same PBS solution wherein additionally is present 7.3 mM sodium taurocholic acid and 1.4 mM of 1-palmitoyl-2-oleyl-sn-glycero-3-phosphocholine. In particular, a composition of the present invention may be dissolution-tested by adding it to MFD or PBS solution and agitating to promote dissolution.

In one aspect, a composition of the present invention, when dosed to an aqueous use environment, provides a maximum drug concentration (MDC) that is at least 1.25-fold that of the MDC provided by a control composition. In other words, if the MDC provided by the control composition is 100 μg/mL, then a composition of the present invention containing a poloxamer provides an MDC of at least 125 μg/mL. Preferably, the MDC of drug provided by the compositions of the present invention is at least 2-fold, more preferably at least 3-fold, and even more preferably at least 5-fold that of the control composition.

When the composition comprises particles of a low-solubility drug and a poloxamer, the control composition is the undispersed drug alone (e.g., the crystalline drug alone in its most thermodynamically stable crystalline form, or in cases where a crystalline form of the drug is unknown, the control may be the amorphous drug alone) or the drug plus a weight of inert diluent equivalent to the weight of poloxamer in the test composition. By "inert" is meant that the diluent is not concentration-enhancing.

When the composition comprises a combination of (1) particles comprising a low-solubility drug and a poloxamer, and (2) a concentration-enhancing polymer, the control composition is the particles alone or the particles plus a weight of inert diluent equivalent to the weight of concentration-enhancing polymer in the test composition.

Alternatively, the compositions of the present invention provide in an aqueous use environment a concentration versus time Area Under the Curve (AUC), for any period of at least 90 minutes between the time of introduction into the use environment and about 270 minutes following introduction to the use environment that is at least 1.25-fold that of the control composition. More preferably, the AUC in the aqueous use environment achieved with the compositions of the present invention are at least 2-fold, more preferably at least 3-fold, and most preferably at least 5-fold that of a control composition.

Alternatively, the compositions of the present invention, when dosed orally to a human or other animal, provide an AUC in drug concentration in the blood plasma or serum that is at least 1.25-fold that observed when an appropriate control composition is dosed. Preferably, the blood AUC is at least about 2-fold, preferably at least about 3-fold, even more preferably at least about 4-fold, still more preferably at least about 6-fold, yet more preferably at least about 10-fold, and most preferably at least about 20-fold that of the control composition. Such compositions may also be said to have a relative bioavailability of from about 1.25-fold to about 20-fold that of the control composition. Thus, the compositions that when evaluated, meet either the in vitro or in vivo or both performance criteria are deemed to be within the scope of this invention.

Alternatively, the compositions of the present invention, when dosed orally to a human or other animal, provide a maximum drug concentration in the blood plasma or serum ($C_{max}$) that is at least 1.25-fold that observed when an appropriate control composition is dosed. Preferably, the blood $C_{max}$ is at least about 2-fold, more preferably at least about 3-fold, even more preferably at least about 4-fold, still more preferably at least about 6-fold, yet more preferably at least about 10-fold, and most preferably at least about 20-fold that of the control composition.

A typical in vitro test to evaluate enhanced drug concentration can be conducted by (1) introducing with agitation a sufficient quantity of test composition (that is, the particles of the low-solubility drug and poloxamer) to a test medium, such that if all of the drug dissolved, the theoretical concentration of drug would exceed the equilibrium concentration of the drug by a factor of at least 2; (2) in a separate test, adding an appropriate amount of control composition to an equivalent amount of test medium; and (3) determining whether the measured MDC and/or AUC of the test composition in the test medium is at least 1.25-fold that provided by the control composition. In conducting such a dissolution test, the amount of test composition or control composition used is preferably an amount such that if all of the drug dissolved, the drug concentration would be at least 2-fold, more preferably at least 10-fold, and most preferably at least 100-fold that of the solubility (that is, the equilibrium concentration) of the drug. For some test compositions of a very low-solubility drug and poloxamer, it may be necessary to administer an even greater amount of the test composition to determine the MDC.

The concentration of dissolved drug is typically measured as a function of time by sampling the test medium and plotting drug concentration in the test medium vs. time so that the MDC and/or AUC can be ascertained. The MDC is taken to be the maximum value of dissolved drug measured over the duration of the test. The aqueous AUC is calculated by integrating the concentration versus time curve over any 90-minute time period between the time of introduction of the composition into the aqueous use environment (when time equals zero) and 270 minutes following introduction to the use environment (when time equals 270 minutes). Typically, when the composition reaches its MDC rapidly, in say less than about 30 minutes, the time interval used to calculate AUC is from time equals zero to time equals 90 minutes. However, if the AUC of a composition over any 90-minute time period described above meets the criterion of this invention, then the composition formed is considered to be within the scope of this invention.

To avoid drug particulates that would give an erroneous determination, the test solution is either filtered or centrifuged. "Dissolved drug" is typically taken as that material that either passes a 0.45 µm syringe filter or, alternatively, the material that remains in the supernatant following centrifugation. Filtration can be conducted using a 13 mm, 0.45 µm polyvinylidine difluoride syringe filter sold by Scientific Resources under the trademark TITAN® Centrifugation is typically carried out in a polypropylene microcentrifuge tube by centrifuging at 13,000 G for 60 seconds. Other similar filtration or centrifugation methods can be employed and useful results obtained. For example, using other types of microfilters may yield values somewhat higher or lower (±10-40%) than that obtained with the filter specified above but will still allow identification of preferred dispersions. It is recognized that this definition of "dissolved drug" encompasses not only monomeric solvated drug molecules but also a wide range of species such as polymer/drug assemblies that have submicron dimensions such as drug aggregates, aggregates of mixtures of polymer and drug, micelles, polymeric micelles, colloidal particles or nanocrystals, polymer/drug complexes, and other such drug-containing species that are present in the filtrate or supernatant in the specified dissolution test.

Alternatively, the compositions of the present invention, when dosed orally to a human or other animal, results in improved bioavailability or an enhanced $C_{max}$. The relative bioavailability and $C_{max}$ of drugs in the compositions can be tested in vivo in animals or humans using conventional methods for making such a determination. An in vivo test, such as a crossover study, may be used to determine whether a composition of drug and poloxamer provides an enhanced relative bioavailability or $C_{max}$ compared with a control composition as described above. In an in vivo crossover study a test composition comprising a low-solubility drug and poloxamer is dosed to half a group of test subjects and, after an appropriate washout period (e.g., one week) the same subjects are dosed with a control composition that consists of an equivalent quantity of crystalline drug as the test composition (but with no poloxamer present). The other half of the group is dosed with the control composition first, followed by the test composition. The relative bioavailability is measured as the concentration of drug in the blood (serum or plasma) versus time area under the curve (AUC) determined for the test group divided by the AUC in the blood provided by the control composition. Preferably, this test/control ratio is determined for each subject, and then the ratios are averaged over all subjects in the study. Likewise, the $C_{max}$ may be determined from the concentration of drug in the blood versus time for the test group divided by that provided by the control composition. In vivo determinations of $C_{max}$ and AUC can be made by plotting the serum or plasma concentration of drug along the ordinate (y-axis) against time along the abscissa (x-axis). To facilitate dosing, a dosing vehicle may be used to administer the dose. The dosing vehicle is preferably water, but may also contain materials for suspending the test or control composition, provided these materials do not dissolve the composition or change the drug solubility in vivo. The determination of $C_{max}$ and AUCs is a well-known procedure and is described, for example, in Welling, "Pharmacokinetics Processes and Mathematics," ACS Monograph 185 (1986).

Excipients and Dosage Forms

Other conventional formulation excipients may be employed in the compositions of this invention, including those excipients well-known in the art, e.g., as described in Remington: *The Science and Practice of Pharmacy* (20$^{th}$ ed., 2000). Generally, excipients such as fillers, disintegrating agents, pigments, binders, lubricants, glidants, flavorants, and so forth may be used for customary purposes and in typical amounts without adversely affecting the properties of the compositions. These excipients may be utilized after the drug/polymer composition has been formed, in order to formulate the composition into tablets, capsules, suppositories, suspensions, powders for suspension, creams, transdermal patches, depots, and the like.

The compositions of the present invention may be delivered by a wide variety of routes, Including, but not limited to, oral, nasal, rectal, vaginal, subcutaneous, intravenous and pulmonary. Generally, oral delivery is preferred.

The compositions of the present invention may be formulated in various forms such that they are delivered as a suspension of particles in a liquid vehicle. Such suspensions may be formulated as a liquid or paste at the time of manufacture, or they may be formulated as a dry powder with a liquid, typically water, added at a later time but prior to oral administration. Such powders that are constituted into a suspension are often termed sachets or oral powder for constitution (OPC) formulations. Such dosage forms can be formulated and reconstituted via any known procedure. The simplest approach is to formulate the dosage form as a dry powder that is reconstituted by simply adding water and agitating. Alternatively, the dosage form may be formulated as a liquid and a dry powder that are combined and agitated to form the oral suspension. In yet another embodiment, the dosage form can be formulated as two powders that are reconstituted by first adding water to one powder to form a solution to which the second powder is combined with agitation to form the suspension.

Generally, it is preferred that the dispersion of drug be formulated for long-term storage in the dry state as this promotes the chemical and physical stability of the drug.

Other features and embodiments of the invention will become apparent from the following examples that are given for illustration of the invention rather than for limiting its intended scope.

EXAMPLES

Examples 1-2

Solid compositions were formed with the glycogen phosphorylase inhibitor 5-chloro-1H-indole-2-carboxylic acid [(1S)-benzyl-(2R)-hydroxy-3-((3R,4S)-dihydroxy-pyrrolidin-1-yl-)-3-oxypropyl]amide ("Drug 1"). This compound has a Log P value of about 2.3; a $T_{g,drug}$ of 113° C. at ambient RH, and a $T_m$ of 216° C.; thus, the $T_m/T_{g,drug}$ ratio (in K/K) for this drug is 1.27. The aqueous solubility of Drug 1 is about 80 μg/mL Example 1 contained 30 wt % Drug 1 and 70 wt % poloxamer 407 (PLURONIC F127, available from BASF Corporation, Mount Olive, N.J.) and Example 2 contained 30 wt % Drug 1 and 70 wt % poloxamer 338 (PLURONIC F108, available from BASF Corporation).

A rotoevaporation process was used to form the solid compositions as follows. First, 0.3 g of Drug 1 and 0.7 g of poloxamer were added to 15 mL methanol in a round-bottom flask, and stirred at room temperature until a clear solution was obtained. Next, the methanol was removed from the solution under vacuum (less than about 0.1 atm), while rotating the flask in a 40° C. bath. The resulting solid composition was dried under vacuum for about 3 hours at room temperature. The dried material was then removed from the flask, chilled in liquid nitrogen, and ground with a mortar and pestle.

The solid compositions of Examples 1-2 were examined to evaluate drug crystallity. Samples were examined using PXRD with a Bruker AXS D8 Advance diffractometer. Samples (approximately 100 mg) were packed in Lucite sample cups fitted with Si(511) plates as the bottom of the cup to give no background signal. Samples were spun in the ψ plane at a rate of 30 rpm to minimize crystal orientation effects. The x-ray source ($KCu_\alpha$, λ=1.54 Å) was operated at a voltage of 45 kV and a current of 40 mA. Data for each sample were collected over a period of 27 minutes in continuous detector scan mode at a scan speed of 1.8 seconds/step and a step size of 0.04°/step. Diffractograms were collected over the 2θ range of 4° to 30°, and showed no indication of crystalline drug—that is the amount of drug in crystalline form was less than the detection limit for the analysis (about 5 wt %). Thus, the drug in the composition was "almost completely amorphous."

The solid compositions of Examples 1-2 were evaluated in an in vitro dissolution test to ascertain concentration enhancement of Drug 1. A 12.0 mg sample of each solid composition was added in duplicate to a microcentrifuge tube, so that the total concentration of Drug 1 would have been 2000 μg/mL if all of the drug had dissolved. The tubes were placed in a 37° C. temperature-controlled chamber, and 1.8 mL PBS containing 0.5 wt % sodium taurocholic acid and 1-palmitoyl-2-oleyl-sn-glycero-3-phosphocholine (NaTC/POPC, with a 4/1 weight ratio) at pH 6.5 and 290 mOsm/kg (simulating a Model Fasted Duodenal solution) was added to each respective tube. The samples were quickly mixed using a vortex mixer for about 60 seconds. The samples were centrifuged at 13,000 G at 37° C. for 1 minute. The resulting supernatant solution was then sampled and diluted 1:6 (by volume) with methanol and then analyzed by high-performance liquid chromatography (HPLC). The contents of each respective tube were mixed on a vortex mixer and allowed to stand undisturbed at 37° C. until the next sample was taken. Samples were collected at 4, 10, 20, 40, 90, and 1200 minutes.

As a control (C1), a sample of crystalline Drug 1 alone was tested in the same manner so that the concentration of Drug 1 in MFD solution would have been 2000 μg/mL if all of the drug had dissolved. The results from the dissolution tests of Examples 1-2 and C1 are shown in Table 1.

TABLE 1

| Example | Time (min) | Drug 1 Concentration (μg/mL) | AUC (min * μg/mL) |
|---|---|---|---|
| 1 | 0 | 0 | 0 |
|   | 4 | 1913 | 3800 |
|   | 10 | 1916 | 15,300 |
|   | 20 | 1911 | 34,500 |
|   | 40 | 1936 | 72,900 |
|   | 90 | 1986 | 171,000 |
|   | 1200 | 1801 | 2,273,000 |
| 2 | 0 | 0 | 0 |
|   | 4 | 1939 | 3900 |
|   | 10 | 1967 | 15,600 |
|   | 20 | 1996 | 35,400 |
|   | 40 | 2034 | 75,700 |
|   | 90 | 2021 | 177,100 |
|   | 1200 | 1079 | 1,897,600 |
| C1 | 0 | 0 | 0 |
|   | 4 | 204 | 400 |
|   | 10 | 227 | 1700 |
|   | 20 | 243 | 4100 |
|   | 40 | 250 | 9000 |
|   | 90 | 255 | 21,600 |
|   | 1200 | 244 | 299,000 |

The concentrations of drug obtained in these samples were used to determine the maximum drug concentration ("$MDC_{90}$") and the area under the concentration-versus-time curve ("$AUC_{90}$") during the initial 90 minutes. The results are shown in Table 2

TABLE 2

| Example | Drug 1 Conc. in Composition (wt % A) | Dissolution Media | $MDC_{90}$ (μg/mL) | $AUC_{90}$ (min * μg/mL) |
|---|---|---|---|---|
| 1 | 30 | MFD | 1986 | 171,000 |
| 2 | 30 | MFD | 2034 | 177,100 |
| C1 (crystalline Drug 1 alone) | 100 | MFD | 255 | 21,600 |

As can be seen from the data, the solid compositions of the present invention provided concentration enhancement relative to crystalline drug alone. Example 1 provided an $MDC_{90}$ that was 7.8-fold that of the crystalline control, and an $ACU_{90}$ that was 7.9-fold that of the crystalline control. Example 2 provided an $MDC_{90}$ that was 8.0-fold that of the crystalline control, and an $AUC_{90}$ was 8.2-fold that of the crystalline control.

Examples 3-4

Solid compositions were formed with the glucocortoid receptor antagonist 2-phenanthrenecarboxamide,4b,5,6,7,8, 8a,9,10-octahydro-7-hydroxy-N-[(2-methyl-3-pyridinyl) methyl]-4b-(phenylmethyl)-7-(3,3,3-trifluoropropyl)-, (4bS, 7S,8aR)-("Drug 2"). This drug has a Log P value of about 6.2; a $T_{g,drug}$ of 99° C. at 0% RH, and a $T_m$ of 225° C.; thus, the $T_m/T_{g,drug}$ ratio (in K/K) for Drug 2 is 1.34. Drug 2 has an aqueous solubility of less than 1 μg/mL. The solid compositions were prepared using the rotoevaporation procedure described for Examples 1 and 2. Example 3 contained 30 wt % Drug 2 and 70 wt % poloxamer 407 (PLURONIC F127, BASF Corporation), and Example 4 contained 30 wt % Drug 2 and 70 wt % poloxamer 338 (PLURONIC F108, BASF Corporation).

The solid compositions of Examples 3-4 were examined using PXRD to evaluate drug crystallinity as described in Examples 1-2. The results demonstrated that Drug 2 in the solid compositions of Examples 3-4 was almost completely amorphous, with no detectable amounts of crystalline Drug 2.

Examples 3-4 were tested by in vitro dissolution tests to ascertain concentration enhancement of Drug 2 as in Examples 1-2, except that a sufficient amount of material was added to the Model Fasted Duodenal solution to obtain a drug concentration of 200 μg/mL if all of the drug dissolved. As a control (C2), crystalline Drug 2 alone was used. The results from these tests are shown in Table 3.

TABLE 3

| Example | Time (min) | Drug 2 Concentration (μg/mL) | AUC (min * μg/mL) |
| --- | --- | --- | --- |
| 3 | 0 | 0 | 0 |
|  | 4 | 113 | 200 |
|  | 10 | 112 | 900 |
|  | 20 | 89 | 1900 |
|  | 40 | 86 | 3700 |
|  | 90 | 54 | 7200 |
|  | 1200 | 2 | 38,700 |
| 4 | 0 | 0 | 0 |
|  | 4 | 106 | 200 |
|  | 10 | 110 | 900 |
|  | 20 | 92 | 1900 |
|  | 40 | 93 | 3700 |
|  | 90 | 83 | 8100 |
|  | 1200 | 4 | 56,500 |
| C2 | 0 | 0 | 0 |
|  | 4 | 1 | 0 |
|  | 10 | 1 | 0 |
|  | 20 | 0 | 0 |
|  | 40 | 0 | 0 |
|  | 90 | 1 | 100 |
|  | 1200 | 5 | 3400 |

The concentrations of drug obtained in these samples were used to determine the $MDC_{90}$ and the $AUC_{90}$ during the initial 90 minutes. The results are shown in Table 4.

TABLE 4

| Example | Drug 2 Conc. in Composition (wt % A) | Dissolution Media | $C_{max90}$ (μg/mL) | $AUC_{90}$ (min * μg/mL) |
| --- | --- | --- | --- | --- |
| 3 | 30 | MFD | 113 | 7200 |
| 4 | 30 | MFD | 110 | 8100 |
| C2 (crystalline Drug 2 alone) | — | MFD | 1 | 100 |

As can be seen from the data, the solid compositions of the invention provided concentration enhancement over that of crystalline drug. The solid composition of Example 3 provided an $MDC_{90}$ that was 113-fold that of the crystalline control, and an $AUC_{90}$ that was 72-fold that of the crystalline control. The solid composition of Example 4 provided an $MDC_{90}$ that was 110-fold that of the crystalline control, and an $AUC_{90}$ that was 81-fold that of the crystalline control.

Examples 5-8

Solid compositions were formed with the retroviral protease inhibitor N-(1,1-dimethylethyl) decahydro-2-[(2R,3R)-2-hydroxy-3-[(3-hydroxy-2-methylbenzoyl)amino]-4-(phenylthio)butyl]-3-isoquinolinecarboxamide (3s, 4aS, 8aS)-monomethanesulfonate, also known as nelfinavir mesylate or VIRACEPT® ("Drug 3"). This drug has a Log P value of about 4.1; a $T_{g,drug}$ of 119° C. at 0% RH and a $T_m$ of 190° C.; thus the $T_m/T_{g,drug}$ ratio (in K/K) is 1.18. The aqueous solubility for Drug 3 is about 6 μg/mL. The solid compositions were made containing 50 wt % Drug 3 and various poloxamers as in Examples 1-2. The materials used to prepare the solid compositions are summarized in Table 5.

TABLE 5

| Example | Drug 3 Mass (g) | Poloxamer* | Poloxamer Mass (g) | Methanol (mL) |
| --- | --- | --- | --- | --- |
| 5 | 0.2593 | Poloxamer 407 (PLURONIC F-127) | 0.2597 | 10 |
| 6 | 0.1046 | Poloxamer 237 (PLURONIC F-87) | 0.1045 | 10 |
| 7 | 0.1070 | Poloxamer 188 (PLURONIC F-68) | 0.1071 | 10 |
| 8 | 0.1142 | Poloxamer 338 (PLURONIC F-108) | 0.1139 | 10 |

*PLURONIC materials obtained from BASF Corporation

The solid composition of Example 5 was examined using PXRD to evaluate drug crystallinity as in Examples 1-2. The results demonstrated that Drug 3 in the solid composition of Example 5 was almost completely amorphous, with no discernable peaks for crystalline Drug 3. The solid composition of Example 5 was stored for three weeks in a controlled atmosphere of 40° C. and 75% RH and showed no evidence of drug crystallization.

Examples 5-8 were tested in in vitro dissolution tests to ascertain concentration enhancement of Drug 3 as in Examples 1-2, except that the dissolution medium was PBS, and a sufficient quantity of the solid composition was added so that the concentration of Drug 3 would have been 1000 μg/mL if all of the drug had dissolved. Crystalline Drug 3 alone (C3) was also tested as a control. The results are shown in Table 6.

TABLE 6

| Example | Time (min) | Drug 3 Concentration (μg/mL) | AUC (min * μg/mL) |
| --- | --- | --- | --- |
| 5 | 0 | 0 | 0 |
|  | 4 | 161 | 300 |
|  | 10 | 143 | 1200 |
|  | 20 | 161 | 2800 |
|  | 40 | 202 | 6400 |
|  | 90 | 262 | 18,000 |
|  | 1200 | 624 | 510,000 |
| 6 | 0 | 0 | 0 |
|  | 4 | 271 | 500 |
|  | 10 | 299 | 2300 |
|  | 20 | 282 | 5200 |
|  | 40 | 305 | 11,000 |

TABLE 6-continued

| Example | Time (min) | Drug 3 Concentration (µg/mL) | AUC (min * µg/mL) |
|---|---|---|---|
|  | 90 | 308 | 26,300 |
|  | 1200 | 469 | 457,900 |
| 7 | 0 | 0 | 0 |
|  | 4 | 41 | 100 |
|  | 10 | 39 | 300 |
|  | 20 | 48 | 800 |
|  | 40 | 70 | 1900 |
|  | 90 | 96 | 6100 |
|  | 1200 | 298 | 225,000 |
| 8 | 0 | 0 | 0 |
|  | 4 | 194 | 400 |
|  | 10 | 209 | 1600 |
|  | 20 | 233 | 3800 |
|  | 40 | 301 | 9100 |
|  | 90 | 273 | 23,500 |
|  | 1200 | 720 | 574,700 |
| C3 | 0 | 0 | 0 |
|  | 4 | 5 | 0 |
|  | 10 | 5 | 0 |
|  | 20 | 6 | 100 |
|  | 40 | 6 | 200 |
|  | 90 | 4 | 400 |
|  | 1200 | 5 | 5100 |

The concentrations of drug obtained in these samples were used to determine the $MDC_{90}$ and the $AUC_{90}$ during the initial 90 minutes. The results are shown in Table 7.

TABLE 7

| Example | Drug 3 Conc. in Composition (wt % A) | Dissolution Media | $C_{max90}$ (µg/mL) | $AUC_{90}$ (min * µg/mL) |
|---|---|---|---|---|
| 5 | 50 | PBS | 262 | 18,000 |
| 6 | 50 | PBS | 308 | 26,300 |
| 7 | 50 | PBS | 96 | 6,100 |
| 8 | 50 | PBS | 301 | 23,500 |
| C3 (crystalline Drug 3) | — | PBS | 6 | 400 |

As can be seen from the data, the solid compositions of the invention provided concentration enhancement over that of crystalline drug. The solid compositions of Example 5-8 provided $MDC_{90}$ values that were 16.0-to 51.3-fold that of the crystalline control, and $AUC_{90}$ values that were 15.3-to 65.8-fold that of the crystalline control.

Example 9

A solid composition of 50 wt % Drug 3 and 50 wt % poloxamer 407 (PLURONIC F127) was prepared by a spray-drying process. A spray solution was formed by dissolving 500.1 mg of Drug 3 and 499.8 mg of PLURONIC F127 into 35 mL of acetone. The solution was pumped into a "mini" spray-drying apparatus via a Cole Parmer 74900 series rate-controlling syringe pump at a rate of 30 mL/hr. The spray solution was atomized through a Spraying Systems Co. two-fluid nozzle, Module No. SU1A using a heated stream of nitrogen (80° C.). The spray solution was sprayed into an 11-cm diameter stainless steel chamber. The resulting solid composition was collected on filter paper, dried under vacuum, and stored in a desiccator. The dispersion was analyzed by PXRD as previously described and no peaks corresponding to crystalline Drug 3 were observed.

The solid composition of Example 9 was tested in an in vitro dissolution test to demonstrate concentration enhancement of Drug 3 as in Examples 5-8. The results are shown in Table 8.

TABLE 8

| Example | Time (min) | Drug 3 Concentration (µg/mL) | AUC (min * µg/mL) |
|---|---|---|---|
| 5 | 0 | 0 | 0 |
|  | 4 | 225 | 450 |
|  | 10 | 210 | 1,750 |
|  | 20 | 205 | 3,820 |
|  | 40 | 165 | 7,530 |
|  | 90 | 200 | 16,700 |
|  | 1200 | 700 | 516,000 |

The concentrations of drug obtained in these samples were used to determine the $MDC_{90}$ and the $AUC_{90}$ during the initial 90 minutes. The results are shown in Table 9, along with the results of crystalline control C3 for comparison.

TABLE 9

| Example | Drug 3 Conc. in Composition (wt % A) | Dissolution Media | $C_{max90}$ (µg/mL) | $AUC_{90}$ (min * µg/mL) |
|---|---|---|---|---|
| 9 | 50 | PBS | 225 | 16,700 |
| C3 (crystalline Drug 3) | — | PBS | 6 | 400 |

As can be seen from the data, the solid composition of Example 9 provided concentration enhancement over that of crystalline drug. The $MDC_{90}$ value was 37.5-fold that of the crystalline control, and the $AUC_{90}$ value was 41.7-fold that of the crystalline control.

Comparative Examples C4 and C5

The Examples demonstrates that forming particles of a low-solubility drug having a low $T_g$ value and a high $T_m/T_{g,drug}$ ratio and a poloxamer results in crsalline drug in the solid composition. A formulation was prepared using the drug nifedipine. nifedipine has a Log P value of about 2.4, a $T_{g,drug}$ of 46° C. at ambient RH, and a $T_m$ of 175° C.; thus the $T_m/T_g$ ratio (in °K/°K) for nifedipine was 1.40. Comparative Example C4 contained 50 wt % nifedipine and 50 wt % poloxamer 407 (PLURONIC F127, BASF Corporation), and Comparative Example C5 contained 25 wt % nifedipine and 75 wt % poloxamer 407 (PLURONIC F127, BASF Corporation).

Formulations were prepared using the procedures outlined in European Patent No. EP0836475B1, as follows. The desired amount of poloxamer 407 was weighed into a glass vial and then stirred and heated to 80° C. until the poloxamer melted. Next, the appropriate amount of nifedipine was gradually added, and the mixture stirred at 80° C. for 2 hours. The resulting mixtures were cooled to room temperature, removed from the vial, chilled in liquid nitrogen, and ground with a mortar and pestle. The resulting materials were analyzed by PXRD using the procedures described above. The diffractograms for both Comparative Examples C4 and C5 showed sharp peaks corresponding to crystalline drug, indicating that at least about 50 wt % of the drug was in the crystalline form.

Examples 10-13

Solid compositions of [2R,4S] 4-[(3,5-bis-trifluoromethyl-benzyl)-methoxycarbonyl-amino]-2-ethyl-6-trifluoromethyl-3,4-dihydro-2H-quinoline-1-carboxylic acid ethyl ester, also known as Torcetrapib ("Drug 4") and the poloxamers PLURONIC F-127 and PLURONIC F-108 (both supplied by BASF) were prepared by a melt-congeal process using the following procedure. Drug 4 has a Log P value of about 7.5, a $T_g$ of about 28° C. at ambient relative humidity and a $T_m$ of about 95° C.; thus, the $T_m/T_g$ ratio (in °K/°K) is 1.2. For each example, the amount of Drug 4 and poloxamer given in Table 10 were accurately weighed and placed into a container. The container was then placed in a hot oil bath maintained at 105° C. After about 15 minutes, the mixture had melted, and was stirred using a magnetic stirrer for about 15 minutes. The molten mixture was transparent, with no apparent color. Next, the container containing the molten mixture was removed from the hot oil bath and placed into liquid nitrogen, resulting in solidification of the molten mixture within a few seconds. The container was removed from the liquid nitrogen after about 60 seconds and allowed to warm to ambient temperature. The resulting opaque solid amorphous composition was then removed from the container using a spatula and broken into small pieces about 1 mm thick. The pieces were then placed into a mortar with some liquid nitrogen and ground into a white powder with a pestle.

TABLE 10

| Example | Concentration of Drug in Polymer (wt %) | Drug Mass (g) | Poloxamer | Polymer Mass (g) |
|---|---|---|---|---|
| 10 | 10 | 0.1003 | Pluronic F-127 | 0.8999 |
| 11 | 25 | 0.2499 | Pluronic F-127 | 0.7502 |
| 12 | 40 | 0.4020 | Pluronic F-127 | 0.6002 |
| 13 | 25 | 0.2494 | Pluronic F-108 | 0.7494 |

The solid compositions of Examples 10-13 were evaluated in an in vitro dissolution test as in Examples 1-2, except that the dissolution medium was PBS. The amount of each composition added to the microcentrifuge tube was adjusted so that the concentration of Drug 4 in solution if all of the drug had dissolved was 1000 µg/mL. The results of these tests are presented in Table 11.

TABLE 11

| Example | Time (min) | Drug 4 Concentration (µg/mL) | AUC (min-µg/mL) |
|---|---|---|---|
| 10 | 0 | 0 | 0 |
|  | 4 | 930 | 1,900 |
|  | 10 | 899 | 7,300 |
|  | 20 | 856 | 16,100 |
|  | 40 | 806 | 32,800 |
|  | 90 | 715 | 70,800 |
|  | 1200 | 385 | 681,700 |
| 11 | 0 | 0 | 0 |
|  | 4 | 699 | 1,400 |
|  | 10 | 653 | 5,500 |
|  | 20 | 594 | 11,700 |
|  | 40 | 551 | 23,100 |
|  | 90 | 438 | 47,900 |
|  | 1200 | 184 | 392,800 |
| 12 | 0 | 0 | 0 |
|  | 4 | 264 | 500 |
|  | 10 | 253 | 2,100 |
|  | 20 | 224 | 4,500 |
|  | 40 | 229 | 9,000 |
|  | 90 | 180 | 19,200 |
|  | 1200 | 90 | 169,100 |
| 13 | 0 | 0 | 0 |
|  | 4 | 542 | 1,100 |
|  | 10 | 496 | 4,200 |
|  | 20 | 459 | 9,000 |
|  | 40 | 397 | 17,500 |
|  | 90 | 318 | 35,400 |
|  | 1200 | 66 | 248,800 |
| Control C6 (Crystalline Drug 4) | 0 | 0 | 0 |
|  | 4 | <1 | <2 |
|  | 10 | <1 | <8 |
|  | 20 | <1 | <18 |
|  | 40 | <1 | <38 |
|  | 90 | <1 | <88 |
|  | 1200 | <1 | <1,200 |

The results are summarized in Table 12, which also includes the data for crystalline Drug 4 alone (Control C6), which was tested under the same conditions. The results show that the $C_{max,90}$ values of the compositions of Examples 10-13 were greater than 262-fold to 930-fold that of the crystalline drug alone, and $AUC_{90}$ values that were greater than 218-fold to 804-fold that of the crystalline drug alone.

TABLE 12

| Example | Poloxamer | Concentration of Drug in Polymer (wt %) | $C_{max,90}$ (µg/mL) | $AUC_{90}$ (min-g/mL) |
|---|---|---|---|---|
| 10 | Pluronic F-127 | 10 | 930 | 70,800 |
| 11 | Pluronic F-127 | 25 | 699 | 47,900 |
| 12 | Pluronic F-127 | 40 | 264 | 19,200 |
| 13 | Pluronic F-108 | 25 | 542 | 35,400 |
| Control C6 | None | — | <1 | <88 |

Examples 14-15

Spray-dried solid compositions of Drug 4 and the poloxamers PLURONIC F-127 and PLURONIC F-108 were prepared by the following procedures. Drug and polymer were first added to acetone and mixed to form a solution. Each solution was pumped into a "mini" spray-drier apparatus via a syringe pump at a rate of 0.7 mL/min. The polymer solution was atomized through a spray nozzle using a stream of nitrogen heated to 90° C. The resulting solid spray-dried composition was collected on a filter paper and dried in a vacuum dessicator. Table 13 summarizes the preparation parameters.

TABLE 13

| Ex. | Drug No. | Concentration of Drug 4 in the Composition (wt %) | Drug Mass (g) | Poloxamer | Polymer Mass (g) | Solvent | Solvent Mass (g) | Spray Apparatus |
|---|---|---|---|---|---|---|---|---|
| 14 | 4 | 25 | 0.2502 | Pluronic F-127 | 0.7501 | Acetone | 116 | mini |

TABLE 13-continued

| Ex. | Drug No. | Concentration of Drug 4 in the Composition (wt %) | Drug Mass (g) | Poloxamer | Polymer Mass (g) | Solvent | Solvent Mass (g) | Spray Apparatus |
|---|---|---|---|---|---|---|---|---|
| 15 | 4 | 25 | 0.0728 | Pluronic F-108 | 0.2199 | Acetone | 44.15 | mini |

The spray-dried compositions of Examples 14-15 were evaluated in an in vitro dissolution test as in Examples 10-13. The amount of each composition added to the microcentrifuge tube was adjusted so that the concentration of Drug 4 in solution if all of the drug had dissolved was 1000 μm/mL. The results of these tests are presented in Table 14.

TABLE 14

| Example | Time (min) | Drug 4 Concentration (μg/mL) | AUC (min-μg/mL) |
|---|---|---|---|
| 14 | 0 | 0 | 0 |
|  | 4 | 508 | 1,000 |
|  | 10 | 449 | 3,900 |
|  | 30 | 420 | 8,200 |
|  | 60 | 371 | 16,100 |
|  | 90 | 272 | 32,200 |
|  | 1200 | 125 | 253,000 |
| 15 | 0 | 0 | 0 |
|  | 4 | 267 | 500 |
|  | 10 | 239 | 2,100 |
|  | 20 | 221 | 4,400 |
|  | 40 | 196 | 8,500 |
|  | 90 | 143 | 17,000 |
|  | 1200 | 36 | 116,200 |

The results are summarized in Table 15, which also includes the data for Control 6, which was tested under the same conditions. The results show that the dissolution, results for the compostions of Examples 14-15 were much better than that of the crystalline drug alone (Control 6), providing $C_{max,90}$ values that were greater than 267-fold and 508-fold that of the crystalline drug alone, respectively, and $AUC_{90}$ values that were greater than 193-fold and 365-fold that of the crystalline drug alone, respectively.

TABLE 15

| Example | Poloxamer | Concentration of Drug in the Composition (wt %) | $C_{max,90}$ (μg/mL) | $AUC_{90}$ (min-μg/mL) |
|---|---|---|---|---|
| 14 | Pluronic F-127 | 25 | 508 | 32,200 |
| 15 | Pluronic F-108 | 25 | 267 | 17,000 |
| Control C6 | None | — | <1 | <88 |

Example 16

A solid amorphous composition comprising 25 wt % Drug 4 in poloxamer 407 (PLURONIC F127) was prepared via a melt-congeal process as in Examples 10-13, with the exceptions noted in Table 16.

TABLE 16

| Example | Concentration of Drug in Polymer (wt %) | Drug Mass (g) | Poloxamer | Polymer Mass (g) |
|---|---|---|---|---|
| 16 | 25 | 1.9997 | Pluronic F-127 | 6.0012 |

This composition was evaluated in an in vitro dissolution test as in Examples 10-13. The results of these tests are presented in Table 17.

TABLE 17

| Example | Time (min) | Drug 4 Concentration (μg/mL) | AUC (min-μg/mL) |
|---|---|---|---|
| 16 | 0 | 0 | 0 |
|  | 4 | 729 | 1,500 |
|  | 10 | 789 | 6,000 |
|  | 20 | 721 | 13,600 |
|  | 40 | 692 | 27,700 |
|  | 90 | 544 | 58,600 |
|  | 1200 | 124 | 429,500 |

The results are summarized in Table 18, which also includes the data for Control C6, which was tested under the same conditions. The results show that the dissolution results for the composition of Example 16 were much better than that of the crystalline drug alone, providing a $C_{max,90}$ value that was greater than 789-fold that of the crystalline drug alone, and an $AUC_{90}$ value that was greater than 665-fold that of the crystalline drug alone.

TABLE 18

| Example | Poloxamer | Concentration Of Drug in Polymer | $C_{max,90}$ (μg/mL) | $AUC_{90}$ (min · μg/mL) |
|---|---|---|---|---|
| 16 | PLURONIC F-127 | 25 | 789 | 58,600 |
| Control C6 | None | — | <1 | <88 |

The composition of Example 16 was used as oral powders for constitution (OPC) for evaluating the performance of the compositions in in vivo tests using male beagle dogs. The OPC was dosed as a suspension in a solution containing 0.5 wt % hydroxypropyl cellulose METHOCEL® (from Dow Chemical Co.), and was prepared as follows. First, 7.5 g of METHOCEL® was weighed out and added slowly to approximately 490 mL of water at 90-100° C. to form a METHOCEL® suspension. After all the METHOCELS® was added, 1000 mL of cool/room temperature water was added to the suspension, which was then placed in an ice water bath. When all of the METHOCEL® had dissolved, 2.55 g of polyoxyethylene 20 sorbitan monooleate (TWEEN 80) were added and the mixture stirred until the TWEEN 80 had dissolved, thus forming a stock suspension solution.

To form the OPC, sufficient quantity of the test composition to result in a 90 mgA amount of Drug 4 was weighed and placed into a mortar. ("mgA" refers to mg of active drug.) A 20 mL quantity of the stock suspension solution was added to the mortar and the test composition was mixed with a pestle. Additional METHOCEL® suspension was added gradually with mixing until a total of 400 mL of the stock suspension solution had been added to the mortar. The suspension was then transferred to a flask, thus forming the OPC. In addition, an OPC containing 90 mgA of amorphous Drug 4 (Control C7) was prepared using the same procedure.

Six male beagle dogs were each dosed with the OPC. On the day of the study, the dogs in a fasted state were dosed with the OPC using a gavage tube and a syringe. Whole blood samples were taken from the jugular vein and analyzed for the concentration of Drug 4 using the following procedure. To 100 μL of each plasma sample, 5 mL of methyl-tert-butyl ether (MTBE) and 1 mL of 500 mM sodium carbonate buffer (pH 9) were added; the sample was vortexed for 1 minute and then centrifuged for 5 minutes. The aqueous portion of the sample was frozen in a dry-ice/acetone bath, and the MTBE layer was decanted and evaporated in a vortex evaporator. Dried samples were reconstituted in 100 μL of mobile phase (33% acetonitrile and 67% of 0.1% formic acid in water). Analysis was carried out by HPLC. The results of these tests are presented in Table 19 and show that the compositions of the present invention provided enhanced drug concentration and enhanced relative bioavailability as compared to the amorphous Drug 4 control (Control C7).

TABLE 19

| Composition | $C_{max}$ (μg/ml) | $AUC_{(0-24)}$ (μg/ml * hr) |
|---|---|---|
| Example 16 (25 wt % Drug 4 in PLURONIC F127) | 544 | 2.1 |
| Control C7 (amorphous Drug 4) | <0.1 | <0.2 |

The composition of Example 16 provided a $C_{max}$ that was more than 5440-fold that of the amorphous control, and a relative bioavailability that was greater than 10.

Comparative Example C8

This Example demonstrates that a solid composition made using a low-solubility drug having a low Tg at high drug loading is not physically stable. A solid composition was prepared consisting of 50 wt % of Drug 4 and 50 wt % poloxamer 407 (PLURONIC F127) using a thermal method. In this method, 4.9 g of the PLURONIC was placed in a glass vial and melted in an oil bath to 110° C. Next, 4.9 g of Drug 4 was added to the molten poloxamer, forming a clear solution. Next, the container containing the molten mixture was removed from the hot oil bath and placed into liquid nitrogen, resulting in solidification of the molten mixture within a few seconds. The container was removed from the liquid nitrogen after about 60 seconds and allowed to warm to ambient temperature. The resulting opaque solid composition was then removed from the container using a spatula and broken into small pieces about 1 mm thick. The pieces were then placed into a mortar with some liquid nitrogen and ground into a white powder using a pestle. Analysis of the solid composition by PXRD showed that a substantial portion of the drug in the composition was amorphous.

The above composition was stored for three weeks in a controlled atmosphere of 40° C. and 25% RH. Analysis of the sample by PXRD showed that about 50 wt % of the drug in the composition had crystallized, clearly indicating physical instability.

Example 17

Particles were formed with (2R)-3-[[3-(4-chloro-3-ethylphenoxy)phenyl][[3-(1,1,2,2-tetrafluoroethoxy)phenyl]methyl]amino]-1,1,1-trifluoro-2-propanol ("Drug 5"). This drug has a Log P value of about 10.0, a $T_{g,drug}$ of about −15° C., a $T_m$ of about 10° C.; thus, the $T_m/T_g$ ratio (in ° K/° K) was 1.1. To form the particles, 125 mg Drug 5 and 500 mg of PLURONIC F127 were weighed into a scintillation vial. A stir bar was added, and the vial was placed in an 80° C. oil bath. The mixture was heated and stirred until the PLURONIC melted and a clear solution was obtained. The mixture was cooled in liquid nitrogen and ground into particles using a mortar and pestle.

The so-formed particles were tested in vitro to ascertain concentration enhancement of Drug 5 as in Examples 1-2 at a dose of 120 μg/mL. Control C9 consisted of amorphous Drug 5 alone. The results from these dissolution tests of the particles of Example 17 and Control C9 are shown in Table 20.

TABLE 20

| Example | Time (min) | Drug 5 Concentration (μg/mL) | AUC (min * μg/mL) |
|---|---|---|---|
| 17 | 0 | 0 | 0 |
|  | 3.5 | 110 | 190 |
|  | 7.25 | 119 | 620 |
|  | 11 | 121 | 1,100 |
|  | 20 | 120 | 2,200 |
|  | 40 | 131 | 4,700 |
|  | 90 | 124 | 11,000 |
|  | 1200 | 115 | 143,800 |
| C9 Amorphous Drug 5 | 0 | 0 | 0 |
|  | 3.5 | 2.8 | 5 |
|  | 7.25 | 3.8 | 17 |
|  | 11 | 5.3 | 34 |
|  | 20 | 8.4 | 96 |
|  | 40 | 15 | 330 |
|  | 90 | 29 | 1,400 |
|  | 1200 | 78 | 60,700 |

The concentration of drug obtained in these samples were used to determine the $C_{max90}$ during the initial 90 minutes. The results are shown in Table 21

TABLE 21

| Example | Drug Conc. in Dispersion. (wt % A) | Media | Dose (μg/mL) | $C_{max90}$ (μg/mL) | $AUC_{90}$ (min * μg/mL) |
|---|---|---|---|---|---|
| 17 | 20 | MFDS | 120 | 131 | 11,000 |
| C9 Amorphous Drug 5 | 100 | MFDS | 120 | 29 | 1,400 |

As can be seen from the data, the composition of Example 17 provided concentration enhancement over that of amorphous drug in that its $C_{max90}$ was 4.5-fold that of the amorphous control, and its $AUC_{90}$ was 7.9-fold that of the amorphous control.

The terms and expressions which have been employed in the foregoing specification are used therein as terms of description and not of limitation, an there is no intention,in the use of such terms and expressions, of excluding equivalents of the features shown and described or portions thereof, it being recognized that the scope of the invention is defined and limited only by the claims which follow.

The invention claimed is:

1. A pharmaceutical composition comprising a mixture that is not a molecular dispersion of the following components:
   (1) at least 50 wt % of particles, said particles comprising a low-solubility drug having a Log P value of greater than 6.5, and a poloxamer, wherein at least 75 wt % of said drug is amorphous; and
   (2) a concentration-enhancing polymer.

2. The composition of claim 1 wherein said concentration-enhancing polymer is selected from the group consisting of hydroxypropyl methyl cellulose acetate succinate, hydroxypropyl methyl cellulose phthalate, cellulose acetate phthalate, cellulose acetate trimellitate, carboxymethyl ethylcellulose, and mixtures thereof.

3. The composition of claim 1 wherein component (1) is a solid solution of said drug homogeneously distributed throughout said poloxamer.

4. The composition of claim 1 or 3 wherein said mixture is a dry physical mixture.

5. The composition of claim 1 or 3 wherein components (1) and (2) of said mixture are present in different regions of said composition.

6. The composition of claim 1 wherein components (1) and (2) of said mixture are present in different layers of a multi-layer tablet.

7. The composition of claim 5 wherein said mixture is present in the same environment of use after components (1) and (2) have been co-administered to said environment of use at a time ranging from approximately the same time to within 60 minutes of each other.

8. The composition of claim 1 or 3 wherein said drug has a glass-transition temperature of at least 50° C.

9. The composition of claim 1 or 3 wherein said drug has a melting point of $T_m$ in K, and wherein said drug has a glass-transition temperature of $T_{g,drug}$, in K, and wherein the ratio of said melting point to said glass transition temperature, $T_m/T_{g,drug}$, is less than 1.4.

10. The composition of claim 1 or 3 wherein said ratio of said melting point to said glass-transition temperature, $T_m/T_{g,drug}$, is less than 1.35.

11. The composition of claim 1 or 3 wherein said ratio of said melting point to said glass-transition temperature, $T_m/T_{g,drug}$, is less than 1.3.

12. A process for preparing a solid composition comprising the steps
   (1) forming a solution consisting essentially of a low-solubility drug, a poloxamer, and a solvent; and
   (2) removing said solvent from said solution to form said solid composition consisting essentially of said low-solubility drug and said poloxamer, at least a substantial portion of said drug in said composition being amorphous;
   wherein said drug has a Log P value greater than 6.5.

13. The process of claim 12 wherein step (2) is selected from the group consisting of spray drying, spray coating, rotoevaporation, and evaporation.

* * * * *